(12) United States Patent
Oode et al.

(10) Patent No.: US 10,582,864 B2
(45) Date of Patent: Mar. 10, 2020

(54) MEASUREMENT SENSOR PACKAGE AND MEASUREMENT SENSOR

(71) Applicant: KYOCERA Corporation, Kyoto-shi, Kyoto (JP)

(72) Inventors: Yasushi Oode, Kirishima (JP); Hiroki Ito, Kirishima (JP); Yoshimasa Sugimoto, Kirishima (JP); Noritaka Niino, Kirishima (JP); Shogo Matsunaga, Kirishima (JP); Takuya Hayashi, Kirishima (JP)

(73) Assignee: KYOCERA CORPORATION, Kyoto-Shi, Kyoto (JP)

( * ) Notice: Subject to any disclaimer, the term of this patent is extended or adjusted under 35 U.S.C. 154(b) by 0 days.

(21) Appl. No.: 16/090,280

(22) PCT Filed: Feb. 22, 2017

(86) PCT No.: PCT/JP2017/006689
§ 371 (c)(1),
(2) Date: Oct. 1, 2018

(87) PCT Pub. No.: WO2017/175504
PCT Pub. Date: Oct. 12, 2017

(65) Prior Publication Data
US 2019/0110697 A1 Apr. 18, 2019

(30) Foreign Application Priority Data

Apr. 4, 2016 (JP) ................... 2016-075079
Jun. 24, 2016 (JP) ................... 2016-126058
Jun. 24, 2016 (JP) ................... 2016-126059

(51) Int. Cl.
*H01L 25/04* (2014.01)
*A61B 5/026* (2006.01)
(Continued)

(52) U.S. Cl.
CPC ............ *A61B 5/0261* (2013.01); *A61B 5/026* (2013.01); *A61B 5/0285* (2013.01); *A61B 5/6826* (2013.01); *A61B 5/6838* (2013.01)

(58) Field of Classification Search
None
See application file for complete search history.

(56) References Cited

U.S. PATENT DOCUMENTS 8,199,518 B1 * 6/2012 Chun ............... H01L 23/49811
361/767
2009/0296762 A1 * 12/2009 Yamaguchi ......... H01S 5/02208
372/34
(Continued)

FOREIGN PATENT DOCUMENTS

JP 5031895 B2 9/2012

*Primary Examiner* — Bradley Smith
(74) *Attorney, Agent, or Firm* — Volpe and Koenig, P.C.

(57) ABSTRACT

A measurement sensor package and a measurement sensor improve reliability in strength and other aspects. A measurement sensor package includes a substrate, a lid, a ground conductor layer, a metallic thin layer, and a bond. The ground conductor layer and the metallic thin layer are arranged inside the bond that extends continuously as viewed through from above. The bond directly bonds a first main surface of a substrate body and a facing surface of the lid together along the entire periphery. This improves the reliability in strength.

18 Claims, 26 Drawing Sheets

(51) Int. Cl.
*A61B 5/0285* (2006.01)
*A61B 5/00* (2006.01)

(56) References Cited

U.S. PATENT DOCUMENTS

| 2011/0092832 | A1 | 4/2011 | Onoe et al. | |
|---|---|---|---|---|
| 2014/0319328 | A1 | 10/2014 | Hsieh | |
| 2018/0017741 | A1* | 1/2018 | Ho | H01S 5/02248 |
| 2018/0310836 | A1* | 11/2018 | Oode | A61B 5/02 |
| 2018/0353087 | A1* | 12/2018 | Oode | A61B 5/0059 |

* cited by examiner

MEASUREMENT SENSOR PACKAGE AND MEASUREMENT SENSOR

FIELD

The present invention relates to a measurement sensor package and a measurement sensor.

BACKGROUND

Measurement sensors that easily and speedily measure biometric information including blood flow have been awaited. Measurement of blood flow uses, for example, the Doppler effect of light. When blood is illuminated with light, the light is scattered by blood cells, such as red blood cells. The frequency of the illuminating light and the frequency of the scattered light are used to calculate the traveling speed of the blood cells.

One example of the measurement sensor for measuring blood flow is a self-luminous measurement sensor described in Patent Literature 1. The sensor includes a substrate, an illuminator arranged on the substrate to illuminate blood with light, a light receiver arranged on the substrate to receive scattered light, and a front plate bonded to the substrate with a light-shielding bond surrounding the illuminator and the light receiver.

The above measurement sensor package and the measurement sensor are touched by a human body and affect the health of the person, and thus are intended to improve reliability in, for example, strength and accuracy.

CITATION LIST

Patent Literature

Patent Literature 1: Japanese Patent No. 5031895

BRIEF SUMMARY

A measurement sensor package according to the present disclosure includes a substrate, a lid, a bond, a ground conductor layer, and a metallic thin layer. The substrate is a plate including a plurality of dielectric layers stacked on one another and has a first surface with a first recess for accommodating a light emitter and a second recess for accommodating a light receiver. The lid covers the first surface of the substrate. The lid is a plate of an insulating material and is optically transmissive. The bond extends continuously along four sides of the first surface of the substrate to bond the first surface of the substrate and a facing surface of the lid facing the first surface together. The bond is light-shielding. The ground conductor layer surrounds an opening of the second recess on the substrate. The ground conductive layer is conductive. The metallic thin layer is on the lid and has an aperture to regulate light receivable by the light receiver.

A measurement sensor according to the present disclosure includes the above measurement sensor package, a light emitter accommodated in the first recess, and a light receiver accommodated in the second recess.

BRIEF DESCRIPTION OF DRAWINGS

The objects, features, and advantages of the present invention will become apparent from the following detailed description and the drawings.

DETAILED DESCRIPTION

A measurement sensor package and a measurement sensor according to the present disclosure will be described with reference to the accompanying drawings. The terms upward and downward (e.g., immediately below) herein are for descriptive purposes, and do not intend to limit the directions in, for example, actual use of the measurement sensor.

First Embodiment

Figure 1:
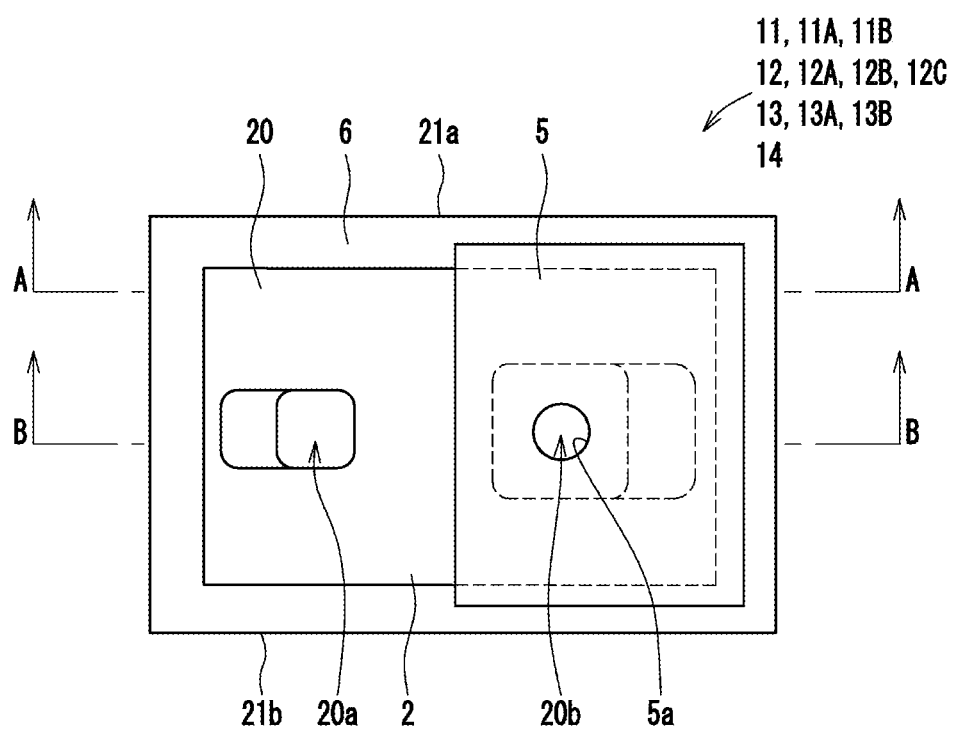
FIG. 1 is a plan view of a measurement sensor package according to the present disclosure.
Figure 2:
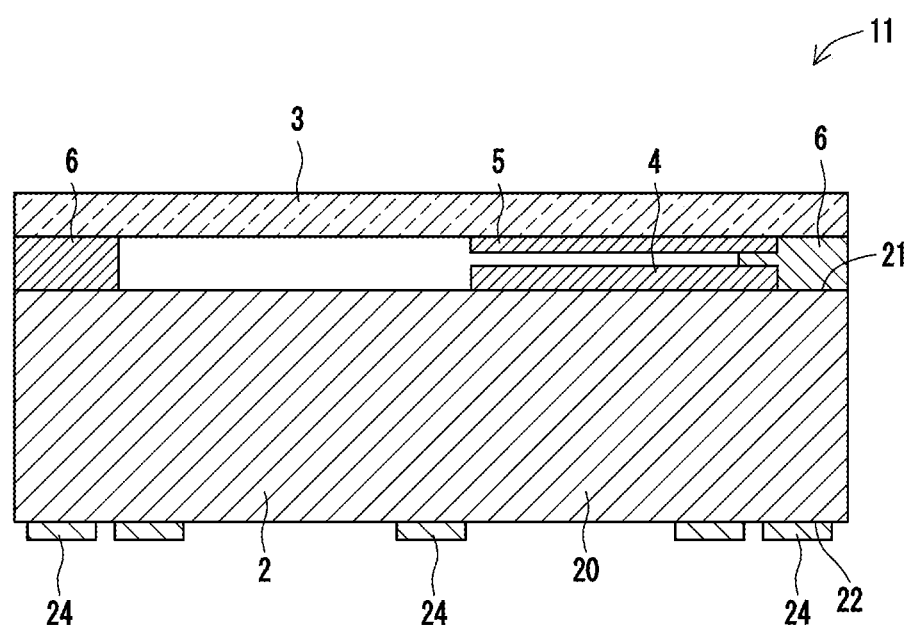
FIG. 2 is a cross-sectional view of a measurement sensor package 11 taken along line A-A of FIG. 1.
Figure 3:
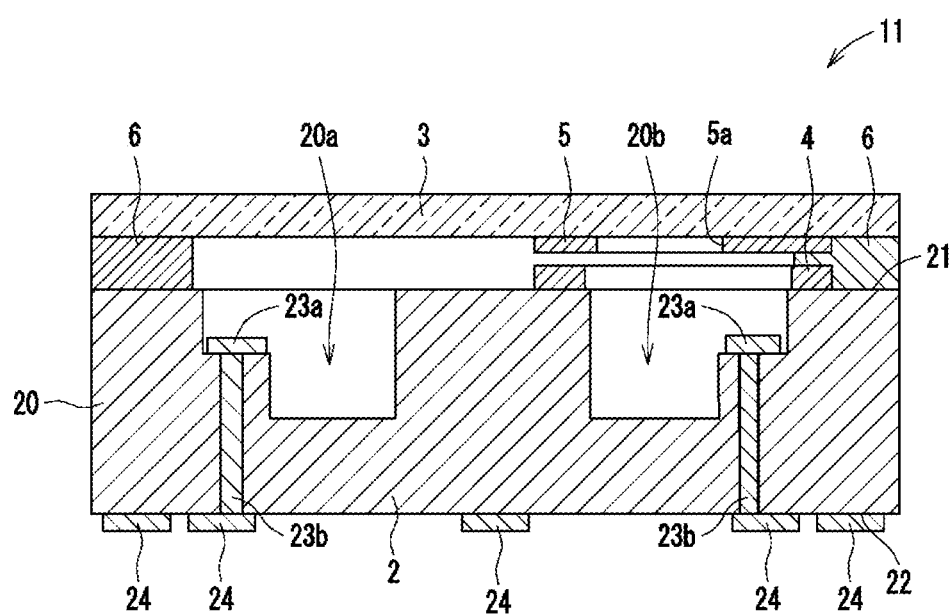
FIG. 3 is a cross-sectional view of the measurement sensor package 11 taken along line B-B of FIG. 1.

FIG. 1 is a plan view of a measurement sensor package 11 according to a first embodiment of the present disclosure. FIG. 2 is a cross-sectional view of the measurement sensor package 11 taken along line A-A of FIG. 1. FIG. 3 is a cross-sectional view of the measurement sensor package 11 taken along line B-B of FIG. 1. In the plan view of FIG. 1, a lid 3 is not shown. The lid 3 is also not shown in a cross-sectional view of each measurement sensor package described later.

The measurement sensor package 11 includes a substrate 2, a lid 3, a ground conductor layer 4, a metallic thin layer 5, and a bond 6. The substrate 2 accommodates a light emitter and a light receiver. The substrate 2 includes a substrate body 20, signal wiring conductors 23, and external connection terminals 24.

The substrate body 20 according to the present embodiment is a rectangular plate, and includes multiple dielectric layers stacked on one another. The substrate body 20 has at least two recesses, which are a first recess 20a for accommodating a light emitter, and a second recess 20b for accommodating a light receiver. The first recess 20a and the second recess 20b are open in the same main surface (first surface of the substrate 2) 21 of the substrate body 20.

The measurement sensor package 11 in the present embodiment may be used for a measurement sensor that measures fluid flow such as blood flow using the Doppler effect of light. To use the Doppler effect of light, the measurement sensor includes a light emitter, which illuminates a measurement object with light, and a light receiver, which receives light scattered by the object. When measuring, for example, blood flow, the measurement sensor package 11 illuminates a body part, such as a finger, with external light, and receives light scattered at blood cells in the blood flowing through blood vessels under the skin to measure the blood flow based on changes in the frequency. Thus, the light emitter and the light receiver are arranged at a predetermined distance from each other in the measurement sensor package 11 based on the positional relationship between the illuminating light and the scattered light. The first recess 20a and the second recess 20b are located in accordance with the positional relationship between the light emitter and the light receiver.

The first recess 20a and the second recess 20b may be sized in accordance with the size of the light emitter and the size of the light receiver to be accommodated in the recesses. When, for example, a vertical cavity surface emitting laser (VCSEL) element is used as the light emitter, the first recess 20a may have a rectangular opening or a square opening, which has, for example, a longitudinal dimension of 0.3 to 2.0 mm, a lateral dimension of 0.3 to 2.0 mm, and a depth of 0.4 to 1.0 mm. When a surface incident photodiode is used as the light receiver, the second recess 20b may have a rectangular opening or a square opening, which has, for example, a longitudinal dimension of 0.3 to 2.0 mm, a lateral dimension of 0.3 to 2.0 mm, and a depth of 0.4 to 1.5 mm.

The first recess 20a and the second recess 20b may each have, for example, a circular, square, or rectangular opening, or an opening having another shape. The first recess 20a and the second recess 20b may each have a uniform cross section parallel to the main surface of the substrate body 20 in the depth direction. As in the cross-sectional view of FIG. 3, the first recess 20a and the second recess 20b may each have a step, or in other words have a cross section that is the same as the opening to a predetermined depth, and then have a smaller uniform cross section from the predetermined depth to the bottom. Each stepped recess as in the present embodiment has the bottom on which the light emitter or the light receiver is mountable, and a step surface on which the connection terminal for electrical connection to the light emitter or the light receiver is to be placed.

Each signal wiring conductor 23 is electrically connected to the light emitter or the light receiver to transmit electric signals input to the light emitter or output from the light receiver. Each signal wiring conductor 23 in the present embodiment includes a bonding wire, which is a connector connected to the light emitter or the light receiver, a connection pad 23a, to which the bonding wire is connected, a signal via conductor 23b, which is electrically connected to the connection pad 23a and extends from immediately below the connection pad to a second main surface 22 of the substrate body 20, and the external connection terminal 24, which is electrically connected to the signal via conductor 23b. Each external connection terminal 24 is arranged on the second main surface 22 of the substrate body 20 and electrically connected, with a terminal bond material such as solder, to a connection terminal on an external mounting board, on which a measurement sensor including the measurement sensor package 11 is mountable.

The external connection terminal 24 may be, for example, plated sequentially with a nickel layer having a thickness of 0.5 to 10 μm and a gold layer having a thickness of 0.5 to 5 μm to improve wettability with the bond, such as solder, and improve corrosion resistance.

The substrate 2, which can contain the light emitter and the light receiver and includes conductors such as the signal wiring conductors 23, may be a ceramic wiring board including the substrate body 20 including dielectric layers formed from a ceramic insulating material, and the signal wiring conductors 23 formed from a conductive material. The substrate 2 may also be an organic wiring board including dielectric layers formed from a resin insulating material.

The substrate 2 that is a ceramic wiring board includes dielectric layers formed from a ceramic material, through which conductors are arranged. The ceramic wiring board is formed from multiple ceramic dielectric layers.

Examples of the ceramic material used for the ceramic wiring board include sintered aluminum oxide, sintered mullite, sintered silicon carbide, sintered aluminum nitride, sintered silicon nitride, and sintered glass ceramic.

The substrate 2 that is an organic wiring board includes insulating layers formed from an organic material, through which conductors are arranged. The organic wiring board is formed from multiple organic dielectric layers.

The organic wiring board may be any wiring board having dielectric layers formed from an organic material, such as a printed wiring board, a build-up wiring board, or a flexible wiring board. Examples of the organic material used for an organic wiring board include an epoxy resin, a polyimide resin, a polyester resin, an acryl resin, a phenol resin, and a fluorine-based resin.

The lid 3 is bonded to the first main surface (the first surface of the substrate 2) 21 of the substrate 2 with the bond 6 to cover the first main surface 21 of the substrate body 20. The lid 3 seals the first and second recesses 20a and 20b accommodating the light emitter and the light receiver. The lid 3 is a plate of an insulating material. The lid 3 transmits light emitted from the light emitter accommodated in the first recess 20a, and light to be received by the light receiver accommodated in the second recess 20b.

The measurement sensor including the measurement sensor package 11 according to the present embodiment illuminates a finger, which is a measurement object, placed on the surface of the lid 3 with light emitted from the light emitter. The lid 3 formed from an electrically conductive material can allow, when the finger touches the lid 3, unintended electric charge accumulating in the finger to be discharged and flow into the substrate 2 through the lid 3, and then generate noise. The lid 3 is formed from an insulating material, and thus does not allow unintended electric charge to flow through the lid 3.

The lid 3 transmits light applied to or scattered by a measurement object. The characteristics of the applied light and the scattered light depend on the light emitter used. The lid 3 may thus at least transmit the light emitted from the light emitter used. The lid 3 may be formed from an insulating material having a light transmittance of at least 70%, or specifically at least 90% for the wavelength of light emitted from the light emitter.

Examples of the insulating material for the lid 3 include a transparent ceramic material such as sapphire, a glass material, and a resin material. Examples of the glass material include borosilicate glass, crystallized glass, quartz, and soda glass. Examples of the resin material include a polycarbonate resin, an unsaturated polyester resin, and an epoxy resin.

The lid 3 is directly touched by a measurement object such as a finger, and thus needs a predetermined strength. The strength of the lid 3 depends on the strength of its material and its thickness. The transparent ceramic material or glass material listed above can have sufficiently high strength when having at least a predetermined thickness. The lid 3 formed from a glass material may have a thickness of, for example, 0.05 to 5 mm.

The ground conductor layer 4 is a metallized layer on the first main surface 21 of the substrate body 20 to surround the opening of the second recess 20b for accommodating the light receiver. The ground conductor layer 4 may have, for example, a rectangular contour in conformance with the contour of the first main surface 21 of the substrate body 20, or may be in any other shape, such as circular or polygonal. The ground conductor layer 4 in the present embodiment has a rectangular contour. The ground conductor layer 4 is a metallized layer surrounding the opening of the second recess 20b. Thus, the ground conductor layer 4 may have a through-hole with at least the same shape as the opening or larger than the opening.

The ground conductor layer 4 is connected to, for example, a ground via conductor such as a ground via (not shown) included in the substrate 2, and receives a ground potential. The ground conductor layer 4 is arranged on the first main surface 21 of the substrate body 20. The ground conductor layer 4 thus on the surface of the substrate 2 is electrically connected to the metallic thin layer 5 with the electrically conductive bond 6. As a result, the metallic thin layer 5 connects to earth for electricity through the ground via. This allows the metallic thin layer to serve as an electric shield against an external charged object (specifically, a measurement object such as a finger), and thus prevent noise from entering a light receiver 31.

The metallic thin layer 5 is formed from a metallic material and is arranged on a facing surface 3a of the lid 3 facing the first main surface 21 of the substrate body 20. In other words, the metallic thin layer 5 is arranged on a main surface opposite to another main surface to be touched by a finger. The metallic thin layer 5 includes an aperture 5a, which is an opening for the light receiver to receive light, and regulates the passage of the light. The size and position of the aperture 5a in the metallic thin layer 5 may be adjusted as appropriate to reduce unintended external light entering the second recess 20b while receiving an amount of light sufficient for measurement. The light receiver receiving unintended external light, such as natural light, outputs an electric signal representing the received amount of unintended light, in addition to the received amount of light reflected by a measurement object, generating optical noise. The aperture 5a reduces such optical noise.

The metallic thin layer 5 also functions as an electromagnetic shield to prevent external electromagnetic waves from entering the second recess 20b. Electromagnetic waves entering the second recess 20b can be received by the signal wiring conductors 23, or in particular bonding wires, which can thus serve as antennas to receive the electromagnetic waves and generate electromagnetic noise. The lid 3 has the thin layer formed from a metallic material on the facing surface 3a, excluding the aperture 5a. This prevents external electromagnetic waves from entering, and thus reduces electromagnetic noise.

The metallic thin layer 5 reduces susceptibility to optical and electrical noise, and improves the measurement accuracy.

The metallic thin layer 5 may be electrically connected to the ground conductor layer 4 and receive a ground potential. In the present embodiment, the metallic thin layer 5 and the ground conductor layer 4 have the contours with the same size.

The metallic thin layer 5 may be formed by, for example, vapor deposition, sputtering, or baking of a metal material including Cr, Ti, Al, Cu, Co, Ag, Au, Pd, Pt, Ru, Sn, Ta, Fe, In, Ni, and W or an alloy of these metals, on the surface of the lid 3 formed from a transparent ceramic material or a glass material. The metallic thin layer 5 has a thickness of, for example, 500 to 4000 Å.

The bond 6 bonds the substrate 2 and the lid 3 together. More specifically, the first main surface 21 of the substrate body 20 and the facing surface 3a of the lid 3 are bonded together on their periphery. The bond 6 is applied continuously along the four sides of the rectangular first main surface 21, and serves as a sealant that provides airtightness and water tightness inside the first and second recesses 20a and 20b in the substrate 2.

The light emitter and the light receiver to be accommodated in the first and second recesses 20a and 20b are susceptible to moisture. The bond 6 is applied continuously along the four sides to prevent entry of external moisture.

The bond 6 is light-shielding. This light-shielding bond 6 prevents external light from entering the first recess 20a or the second recess 20b through the gap between the substrate 2 and the lid 3.

The bond 6 may absorb light for light-shielding. The bond 6 may reflect light for light-shielding to prevent entry of external light. However, the bond 6 in this case may reflect any stray light inside the measurement sensor, which may then be received by the light receiver. The bond 6 that absorbs light prevents entry of external light and also absorbs internally occurring stray light.

The bond 6 may be formed from materials including a material that absorbs light for light-shielding. The bond 6 may be formed from a material containing a resin adhesive, such as an epoxy resin and a conductive silicone resin, which bonds the substrate 2 and the lid 3 together. The bond 6 additionally contains a light-absorbing material in a dispersed manner. Examples of the light-absorbing material include inorganic pigments. Examples of the inorganic pigments include carbon pigments such as carbon black, nitride pigments such as titanium black, and metal oxide pigments such as Cr—Fe—Co, Cu—Co—Mn, Fe—Co—Mn, and Fe—Co—Ni—Cr pigments.

In the present embodiment, the ground conductor layer 4 and the metallic thin layer 5 are arranged inside the periphery of the bond 6 extending continuously as viewed through from above. In other words, the ground conductor layer 4 and the metallic thin layer 5 partially extend in the area between the first main surface 21 of the substrate body 20 and the facing surface 3a of the lid 3. The lid 3 and the substrate 2 are directly bonded together along the entire periphery by the bond 6. The bond 6 may partially overlap the ground conductor layer 4 or the metallic thin layer 5.

The substrate 2 and the lid 3 bonded together can increase the bonding strength in the area without the ground conductor layer 4 and the metallic thin layer 5 between them, and thus prevent, for example, the lid 3 from coming off.

Figure 4:
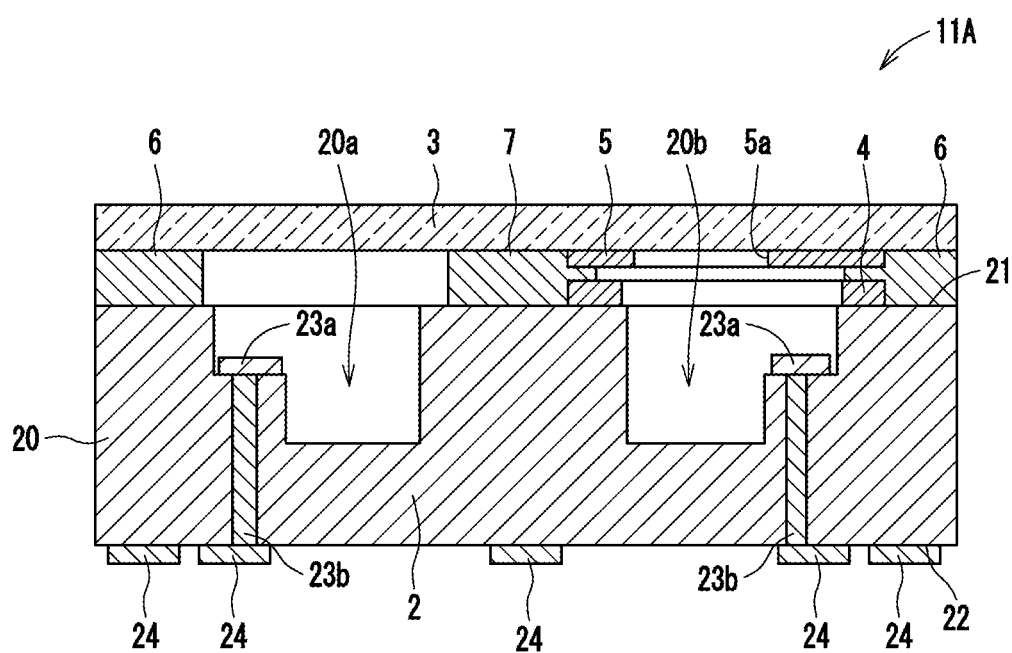
FIG. 4 is a cross-sectional view of a measurement sensor package 11A corresponding to the cross-sectional view of FIG. 3.
Figure 5:
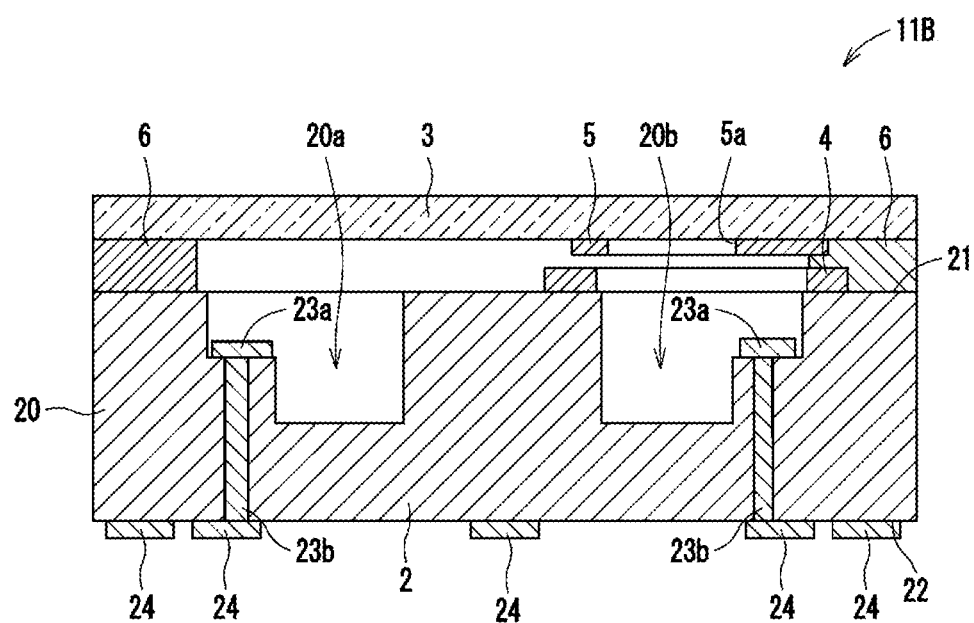
FIG. 5 is a cross-sectional view of a measurement sensor package 11B corresponding to the cross-sectional view of FIG. 3.

Other examples of the present embodiment will now be described. FIG. 4 is a cross-sectional view of a measurement sensor package 11A corresponding to the cross-sectional view of FIG. 3. FIG. 5 is a cross-sectional view of a measurement sensor package 11B corresponding to the cross-sectional view of FIG. 3.

The measurement sensor package 11A according to another example basically has the same structure as the measurement sensor package 11 according to the above embodiment except that the measurement sensor package 11A further includes a partition 7. The same components are given the same reference signs as for the measurement sensor package 11, and will not be described in detail.

The partition 7 in the measurement sensor package 11A is a strip on a first main surface (first surface of a substrate 2) 21 of a substrate body 20. The partition 7 is light-shielding. The partition 7 is located between a first recess 20a and a second recess 20b, and extends from a first side 21a of the first main surface 21 toward a second side 21b parallel to the first side 21a. In the present embodiment, the first recess 20a and the second recess 20b are arranged in parallel in the longitudinal direction of the first main surface 21. Thus, the first side 21a and the second side 21b are the long sides parallel to each other.

The partition 7 separates the first recess 20a from the second recess 20b. Light emitted from a light emitter may be reflected on a facing surface 3a of a lid 3 without passing through the lid 3. Such light may then be repeatedly reflected between the facing surface 3a of the lid 3 and the first main surface 21 of the substrate body 20, and reach the second recess 20b. Stray light generated in this manner may be received by the light receiver, and may thus cause optical noise.

The partition 7 between the first and second recesses 20a and 20b prevents such stray light, which is from light emitted from the light emitter, from reaching the second recess 20b. This reduces optical noise.

The partition 7 may be formed from the same materials as for the bond 6. The partition 7 using the same material as for the bond 6 can be formed through the same manufacturing processes as for the bond 6. The partition 7 may have the same height as the bond 6. This structure allows portions of the substrate 2 and the lid 3 to be bonded together between the first and second recesses 20a and 20b, and thus increases the bonding strength further.

In this example, the partition 7 separates the first recess 20a from the second recess 20b. The ground conductor layer 4 and the metallic thin layer 5 are thus arranged only in the segment including the second recess 20b separated by the partition 7 from the segment including the first recess 20a.

The measurement sensor package 11B according to still another example basically has the same structure as the measurement sensor package 11 except that a metallic thin layer 5 has a smaller contour than a ground conductor layer 4 as viewed through from above. The same components are given the same reference signs as for the measurement sensor package 11, and will not be described in detail.

Although the contour of the metallic thin layer 5 has the same size as the contour of the ground conductor 4 for measurement sensor package 11 according to the above embodiment, the contour of a metallic thin layer 5 is smaller than the contour of a ground conductor layer 4 in the present example. In other words, the metallic thin layer 5 extends within the range of the entire ground conductor layer 4 when viewed through from above.

In this manner, the metallic thin layer 5 with a smaller contour than the ground conductor layer 4 has electric capacity with the ground conductor layer 4 less susceptive to positional deviation, and thus has stable characteristics. Further, the bonded structure between the metallic thin layer 5 smaller than the ground conductor layer 4 is visually observable. This facilitates inspection of the sealed state.

A method for manufacturing the measurement sensor package 11 will now be described. First, the substrate 2 is fabricated with a method similar to known methods used for manufacturing multi-layer wiring boards. For the substrate 2 that is a ceramic wiring board using alumina as a ceramic material, the powders of raw materials such as alumina ($Al_2O_3$), silica ($SiO_2$), calcium oxide (CaO), and magnesia (MgO) are mixed with an appropriate organic binder and an appropriate solvent to form slurry. The slurry is then shaped into a sheet using a known method such as a doctor blade or by calendering to obtain a ceramic green sheet (hereafter also referred to as a green sheet). The green sheet then undergoes punching into a predetermined shape. The powders of raw materials such as tungsten (W) and a glass material are mixed with an organic binder and a solvent to form a metal paste. The metal paste is then applied in a predetermined pattern by, for example, screen printing on the surface of the green sheet. The green sheet has through-holes formed and filled with the metal paste by, for example, screen printing to form via conductors. The metallized layer to be the ground conductor layer 4 is formed on an outermost surface with the metal paste. Multiple green sheets prepared in this manner are stacked on one another, and then fired together at about 1600° C. to complete the substrate 2.

The lid 3 is prepared by, for example, machining or cutting a glass material into a predetermined shape. The metallic thin layer 5 is formed on the facing surface 3a of the lid 3 by, for example, vapor deposition, sputtering, or baking. The aperture 5a can be formed by patterning the metal thin layer by, for example, photolithography (wet etching) or dry etching.

Figure 6:
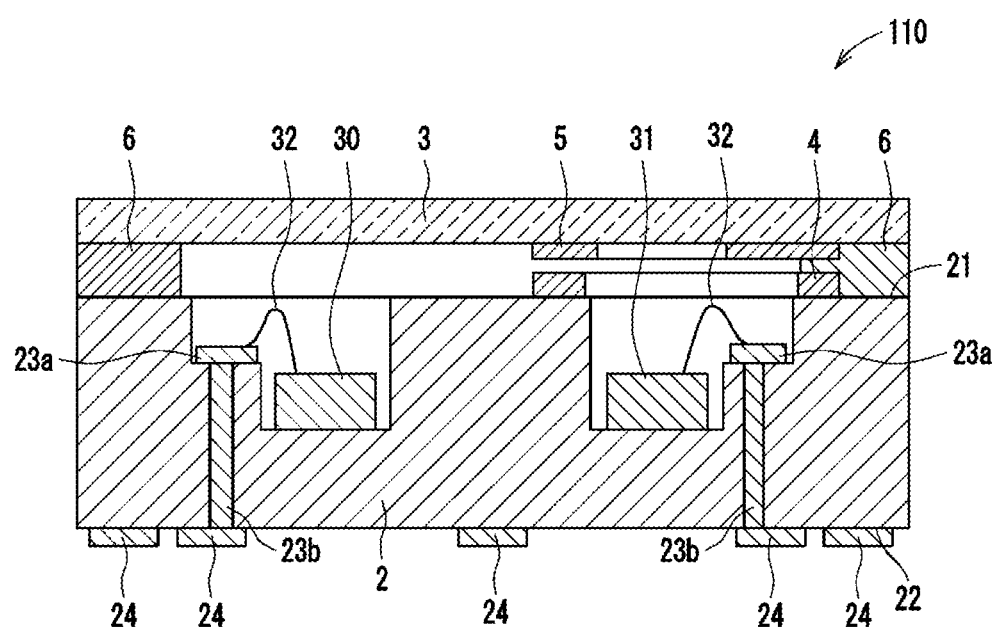
FIG. 6 is a cross-sectional view of a measurement sensor 110 showing its structure.

A measurement sensor 110 according to still another example of the present embodiment will now be described. FIG. 6 is a cross-sectional view of the measurement sensor 110 showing its structure. The measurement sensor 110 includes the measurement sensor package 11, 11A, or 11B, a light emitter 30 accommodated in a first recess 20a, and a light receiver 31 accommodated in a second recess 20b. The measurement sensor 110 is obtained by mounting the light emitter 30 and the light receiver 31 on the measurement sensor package 11 and connecting the light emitter 30 and the light receiver 31 to connection pads 23a both using bonding wires 32, and joining a lid 3 to a substrate body 20 with a bond 6.

The light emitter 30 may be formed from a semiconductor laser element such as a VCSEL. The light receiver 31 may be formed from a photodiode such as a silicon photodiode, a GaAs photodiode, an InGaAs photodiode, or a germanium photodiode. The light emitter 30 and the light receiver 31 may be appropriately selected in accordance with the type of a measurement object or the parameters to be measured.

For example, a VCSEL that can emit a laser beam with a wavelength of 850 nm may be used as the light emitter 30 for measuring blood flow using the optical Doppler effect. To measure another object, another device that emits a laser beam with a wavelength appropriate for the measurement object may be selected as the light emitter 30. The light receiver 31 may be any light receiver that can receive a laser beam emitted from the light emitter 30 when the wavelength of the laser beam emitted from the light emitter 30 remains unchanged. When the wavelength of the laser beam emitted from the light emitter 30 changes, the light receiver 31 is to be a light receiver that can receive a light beam with the changed wavelength.

Although the light emitter 30 and the light receiver 31 are electrically connected to the connection pads 23a with, for example, the bonding wires 32 in the present embodiment, the connection may be achieved with another method, such as flip chip connection, a method using bumps, or a method using an anisotropic conductive film.

The measurement sensor 110 is mounted on an external mounting board for use. For example, a control unit for controlling light emission from the light emitter 30, and an arithmetic unit that calculates the blood flow rate and other parameters based on signals output from the light receiver 31 are also mounted on the external mounting board.

To start measurement, the fingertip of a finger, which is a measurement object, is placed into contact with the surface of the lid 3, and a light emitter control current is input from the external mounting board into the measurement sensor 110 through the external connection terminal 24, and input to the light emitter 30 through a signal via conductor 23b and the connection pad 23a. Light for measurement is then emitted from the light emitter 30. When the emitted light is applied to the fingertip through the lid 3, the light is scattered by blood cells in the blood. When receiving the scattered light transmitted through the lid 3 and passing through an aperture 5a, the light receiver 31 outputs an electric signal corresponding to the amount of received light. The output signal then passes through the connection pad 23a and the signal via conductor 23b, and is output from the measurement sensor 110 to the external mounting board through the external connection terminal 24.

In the external mounting board, a signal output from the measurement sensor 110 is input to the arithmetic unit, which can then calculate the blood flow rate based on, for example, the frequency of the illuminating light emitted from the light emitter 30 and the frequency of the scattered light received by the light receiver 31.

In the above structure, the signal via conductors 23b vertically extend linearly in the substrate body 20. The signal via conductors 23b may not extend linearly, and may be displaced inside the substrate body 20 due to, for example, an inner layer wire or an internal ground conductor layer when the substrate body 20 has a first main surface 21 electrically connected to the external connection terminals 24 on a second main surface 22.

The substrate 2 may include a ground via conductor extending through the substrate body 20 in the thickness direction. The ground via conductor is electrically connected to, for example, the ground conductor layer 4 and the external connection terminal 24, and arranged outside the first and second recesses 20a and 20b in the substrate body 20. The ground via conductor guides electric charge from a human finger as a measurement object touching the measurement sensor from the first main surface 21 to the second main surface 22 of the substrate body 20, and then outside.

This structure defines a path that allows electric charge from a human to easily flow in the measurement sensor package 11 to guide the electric charge on the path and then outside. This reduces electrical noise.

Second Embodiment

Figure 7:
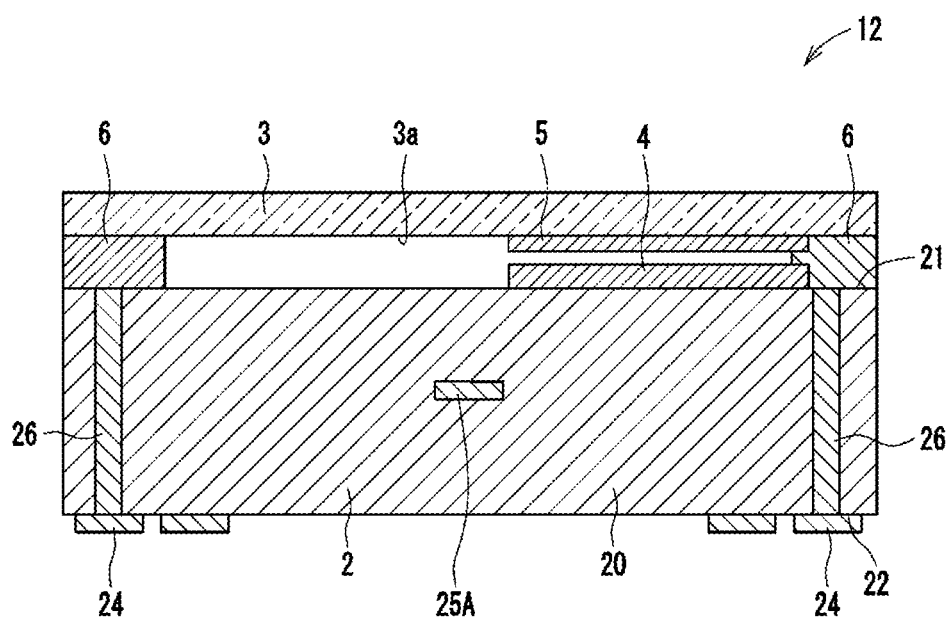
FIG. 7 is a cross-sectional view of a measurement sensor package 12 taken along line A-A of FIG. 1.
Figure 8:
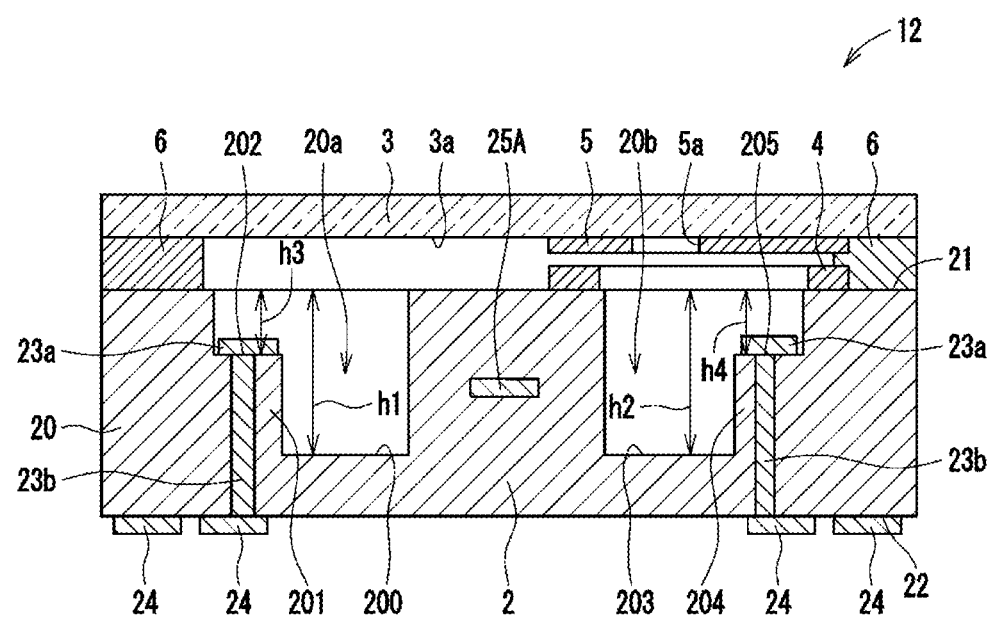
FIG. 8 is a cross-sectional view of the measurement sensor package 12 taken along line B-B of FIG. 1.
Figure 9:
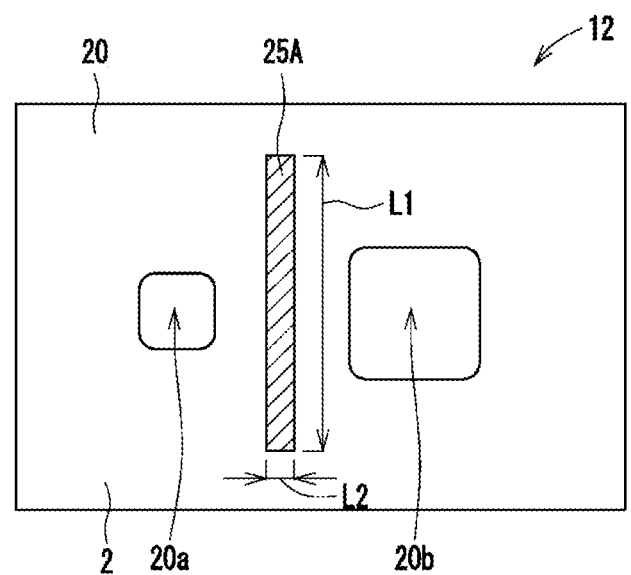
FIG. 9 is a perspective plan view of the measurement sensor package 12.

FIG. 1 is a plan view of a measurement sensor package 12 according to a second embodiment of the present disclosure. FIG. 7 is a cross-sectional view of the measurement sensor package 12 taken along line A-A of FIG. 1. FIG. 8 is a cross-sectional view of the measurement sensor package 12 taken along line B-B of FIG. 1. FIG. 9 is a perspective plan view of the measurement sensor package 12.

The measurement sensor package 12 includes a substrate 2, a lid 3, and a first internal ground conductor layer 25A. The substrate 2 accommodates a light emitter and a light receiver. The substrate 2 includes a substrate body 20, signal wiring conductors 23, and external connection terminals (or external ground terminals) 24.

The measurement sensor package 12 according to the present embodiment differs from the measurement sensor package 11 according to the above embodiment except that the first internal ground conductor layer 25A is included to shield the light receiver from electromagnetic noise from the light emitter. The measurement sensor package 12 has the same other components. The same components are given the same reference signs as for the measurement sensor package 11, and will not be described in detail.

First Example

The measurement sensor package 12 according to the present embodiment has basically the same structure as the above measurement sensor package 11, and may be used for a measurement sensor that measures fluid flow such as blood flow using the Doppler effect of light.

As shown in FIG. 8, the measurement sensor package 12 according to the present embodiment includes a first recess 20a with a first bottom surface 200, on which the light emitter is mountable, and a second recess 20b with a second bottom surface 203, on which the light receiver is mountable. The first recess 20a has an inner side surface having a first step 201 with a first step surface 202, which receives a connection pad (or an electrode pad) 23a electrically connectable to the light emitter. The second recess 20b has an inner side surface having a second step 204 with a second step surface 205, which receives a connection pad 23a electrically connectable to the light receiver. The measurement sensor package 12 has the first and second bottom surfaces 200 and 203 at the same distance from a first main surface 21, and has the first and second step surfaces 202 and 205 at the same distance from the first main surface 21. The first main surface 21 is a flat surface of the substrate body 20 excluding the openings of the first and second recesses 20a and 20b. The first main surface 21 is at a distance h1 from the first bottom surface 200, which is a flat surface, and at a distance h2 from the second bottom surface 203, which is a flat surface. The distances h1 and h2 are the same. In other words, the first recess 20a and the second recess 20b have the same depth. The first step surface 202 and the second step surface 205 are both flat surfaces. The first and second step surfaces 202 and 205 are at the same distances h3 and h4 from the first main surface 21. In other words, the first step 201 and the second step 204 have the same depth. The distances h1 and h2 being the same include the distances h1 and h2 having a difference between them that falls within ±10% ($0.9 \leq (h2/h1) \leq 1.1$), in addition to the value h1 being equal to the value h2 ($(h2/h1)=1$). The same applies to distances h3 and h4.

A measurement sensor including the measurement sensor package 12 according to the present embodiment illuminates a finger, which is a measurement object, placed on the surface of the lid 3 with light emitted from the light emitter. In the measurement sensor package 12, similarly to the above measurement sensor package 11, the lid 3 may be formed from an insulating material, and thus does not allow unintended electric charge to flow through the lid 3.

The first internal ground conductor layer 25A is arranged between the dielectric layers included in the substrate body 20, and specifically between the first recess 20a and the second recess 20b as viewed through from above. The first internal ground conductor layer 25A formed from a conductive material is electrically connected to ground via conductors 26, which are electrically connected to the external connection terminals 24, in the substrate body 20 and receives a ground potential. Thus, the first internal ground conductor layer 25A functions as an electromagnetic shield.

A self-luminous measurement sensor includes a light emitter that emits light to be scattered by a measurement object, and a light receiver that receives light scattered by the measurement object. When the optical path from the light emitter to the light receiver is shorter, the right receiver typically receives more light, thus increasing the sensitivity of the measurement sensor. However, when the light emitter and the light receiver are arranged close to each other, any electromagnetic noise in the light emitter easily enters the light receiver and degrades the measurement accuracy of the measurement sensor. In particular, a measurement sensor used for measuring blood flow or other purposes includes a light receiver that receives a relatively small amount of light and outputs a weak electric signal. This measurement sensor is susceptible to electromagnetic noise.

The measurement sensor package 12 according to the present embodiment includes the first bottom surface 200, on which the light emitter is mountable, and the second bottom surface 203, on which the light receiver is mountable, arranged close to each other as shown in FIGS. 1 and 8. The first internal ground conductor layer 25A is arranged between the first recess 20a and the second recess 20b as viewed through from above to shield the light receiver from electromagnetic noise from the light emitter. The measurement sensor package 12 according to the present embodiment reduces electric crosstalk between the light emitter and the light receiver, and thus improves the accuracy of measurement.

The measurement sensor package 12 also includes the first internal ground conductor layer 25A arranged between the first recess 20a and the second recess 20b as viewed through from above, and between the first bottom surface 200 and the first step surface 202 as viewed through laterally. In other words, the first internal ground conductor layer 25A is arranged on a path through which any electromagnetic noise in the light emitter propagates toward the light receiver. Thus, the measurement sensor package 12 effectively prevents any electromagnetic noise in the light emitter from entering the light receiver through a portion separating the first recess 20a and the second recess 20b in the substrate body 20. This effectively reduces electric crosstalk between the light emitter and the light receiver.

The first internal ground conductor layer 25A may be, for example, circular, square, or rectangular, or in any other shape as viewed through from above. The first internal ground conductor layer 25A according to the present embodiment shown in FIG. 9 is elongated in a direction intersecting with a direction linking the centroids of the first and second recesses 20a and 20b as viewed through from above. In other words, the first internal ground conductor layer 25A has a greater length L1 in the direction intersecting with the direction linking the centroids of the first and second recesses 20a and 20b, and a smaller length L2 in the direction linking the centroids of the first and second recesses 20a and 20b as viewed through from above. The ratio L1/L2 of the length L1 to the length L2 may be 2.0 to 10.0. This structure effectively prevents any electromagnetic noise in the light emitter from entering the light receiver, and thus effectively reduces electric crosstalk between the light emitter and the light receiver.

The first internal ground conductor layer 25A may extend in a direction perpendicular to the direction linking the centroids of the first and second recesses 20a and 20b as viewed through from above. The length L1 of the first internal ground conductor layer 25A may be greater than the length of each of the first recess 20a and the second recess 20b in the direction perpendicular to the direction linking the centroids of the first and second recesses 20a and 20b as viewed through from above.

The measurement sensor package 12 according to the present embodiment further includes the signal wiring conductors 23. Each signal wiring conductor 23 is electrically connected to the light emitter or the light receiver to transmit electric signals input to the light emitter or output from the light receiver. Each signal wiring conductor 23 in the present embodiment includes a bonding wire, which is a connector connected to the light emitter or the light receiver, a connection pad 23a, to which the bonding wire is connected, a signal via conductor 23b, which is electrically connected to the connection pad 23a and extends from immediately below the connection pad to a second main surface 22 of the substrate body 20, and the external connection terminal 24, which is electrically connected to the signal via conductor 23b. Each external connection terminal 24 is arranged on the second main surface 22 of the substrate body 20 and electrically connected, with a terminal bond material such as solder, to a connection terminal on an external mounting board, on which a measurement sensor including the measurement sensor package 12 is mountable.

The external connection terminal 24 may be, for example, plated sequentially with a nickel layer having a thickness of 0.5 to 10 μm and a gold layer having a thickness of 0.5 to 5 µm to improve wettability with the bond, such as solder, and improve corrosion resistance.

The measurement sensor package 12 according to the present embodiment may further include a ground conductor layer (or a lid ground conductor layer) 4, a metallic thin layer 5, and a bond (or a conductive bond) 6.

The ground conductor layer 4 is a metallized layer on the first main surface 21 of the substrate body 20 to surround the opening of the second recess 20b for accommodating the light receiver. The ground conductor layer 4 may have, for example, a rectangular contour in conformance with the contour of the first main surface 21 of the substrate body 20, or may be in any other shape, such as circular or polygonal. The ground conductor layer 4 in the first embodiment has a rectangular contour. The ground conductor layer 4 is a metallized layer surrounding the opening of the second recess 20b. Thus, the ground conductor layer 4 may have a through-hole with at least the same shape as the opening or larger than the opening.

The ground conductor layer 4 is connected to a ground via conductor such as a ground via (not shown) included in the substrate 2, and receives a ground potential.

The metallic thin layer 5 may be electrically connected to the ground conductor layer 4 and receive a ground potential. In the first embodiment, the metallic thin layer 5 and the ground conductor layer 4 have the contours with the same size.

In the present embodiment, the ground conductor layer 4 and the metallic thin layer 5 are arranged inside the bond 6 extending continuously as viewed through from above. In other words, the first main surface 21 of the substrate body 20 and the facing surface 3a of the lid 3 are directly bonded together by the bond 6 along the entire periphery without the ground conductor layer 4 and the metallic thin layer 5 between them.

The substrate 2 and the lid 3 bonded together without the ground conductor layer 4 and the metallic thin layer 5 between them increase their bonding strength, and thus prevent, for example, the lid 3 from coming off.

Second Example

Figure 10:
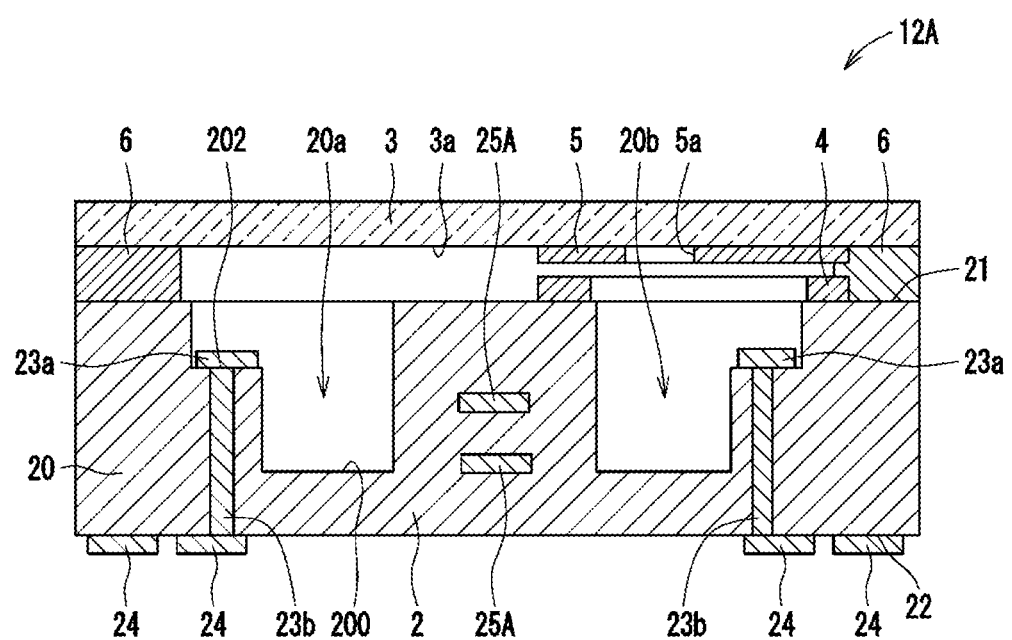
FIG. 10 is a cross-sectional view of a measurement sensor package 12A according to a second example of a second embodiment corresponding to the cross-sectional view of FIG. 8.

Another example of the present embodiment will now be described. FIG. 10 is a cross-sectional view of a measurement sensor package 12A according to a second example corresponding to the cross-sectional view of FIG. 8.

The measurement sensor package 12A according to the second example basically has the same structure as the measurement sensor package 12 according to the above embodiment except that the measurement sensor package 12A includes multiple first internal ground conductor layers 25A. The same components are given the same reference signs as for the measurement sensor package 12, and will not be described in detail.

The measurement sensor package 12A according to the second example includes multiple first internal ground conductor layers 25A between a first bottom surface 200 and a first step surface 202 as viewed through laterally. Compared with the measurement sensor package 12, the measurement sensor package 12A further improves the shielding against electromagnetic noise using the multiple first internal ground conductor layers 25A, and thus further improves the accuracy of measurement.

Although the structure in FIG. 10 includes two first internal ground conductor layers 25A, the structure may include more first internal ground conductor layers 25A, or specifically more than two first internal ground conductor layers 25A between the first bottom surface 200 and the first step surface 202. The multiple first internal ground conductor layers 25A may be shaped differently as viewed through from above. The multiple first internal ground conductor layers 25A may be displaced from one another or overlap one another as viewed through from above.

Third Example

Figure 11:
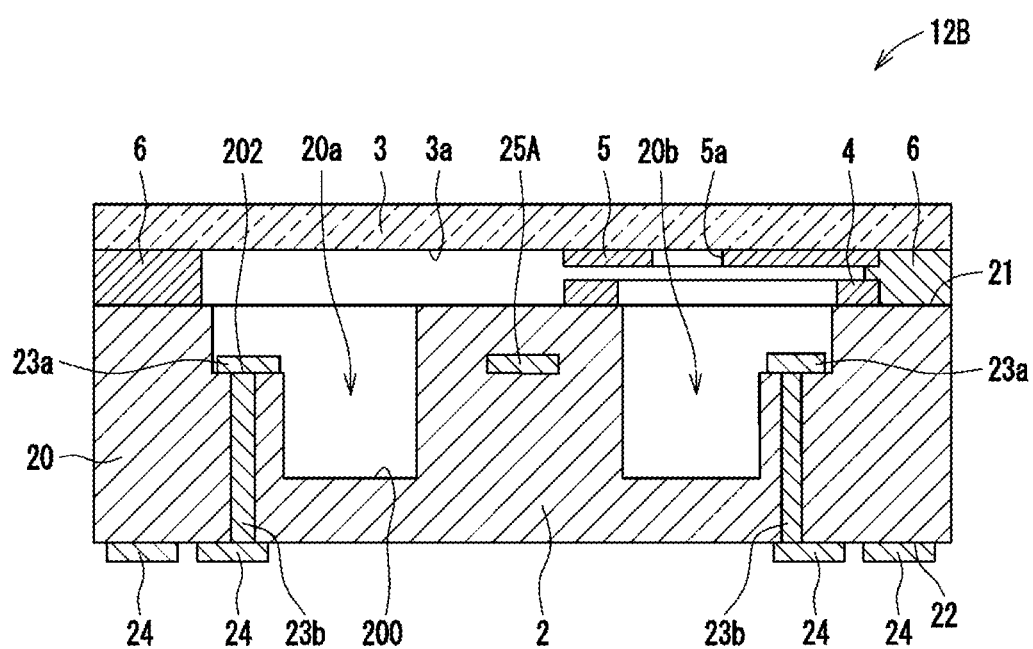
FIG. 11 is a cross-sectional view of a measurement sensor package 12B according to a third example of the second embodiment corresponding to the cross-sectional view of FIG. 8.

FIG. 11 is a cross-sectional view of a measurement sensor package 12B according to a third example corresponding to the cross-sectional view of FIG. 8.

The measurement sensor package 12B according to the third example basically has the same structure as the measurement sensor package 12 except that a first internal ground conductor layer 25A is at a different position as viewed through laterally. The same components are given the same reference signs as for the measurement sensor package 12, and will not be described in detail.

The measurement sensor package 12B according to the third example includes the first internal ground conductor layer 25A between a first surface of a substrate body 20 and a first step surface 202 as viewed through laterally. As described above, the first step surface 202 and a second step surface 205 have connection pads 23a for electrical connection to a light emitter or a light receiver. When the connection pad 23a and the light emitter or the light receiver are electrically connected with a bonding wire, the bonding wire is exposed. This may cause electromagnetic noise in a current flowing in the bonding wire connecting the connection pad 23a to the light emitter to enter the light receiver. This may cause electric crosstalk between the light emitter and the light receiver.

The measurement sensor package 12B according to the third example includes a first internal ground conductor layer 25A between the first surface of the substrate body 20 and the first step surface 202 as viewed through laterally. This prevents any electromagnetic noise in the bonding wire from entering the light receiver. Although the structure in FIG. 11 includes the single first internal ground conductor layer 25A, the structure may include multiple first internal ground conductor layers 25A between the first surface of the substrate body 20 and the first step surface 202.

Fourth Example

Figure 12:
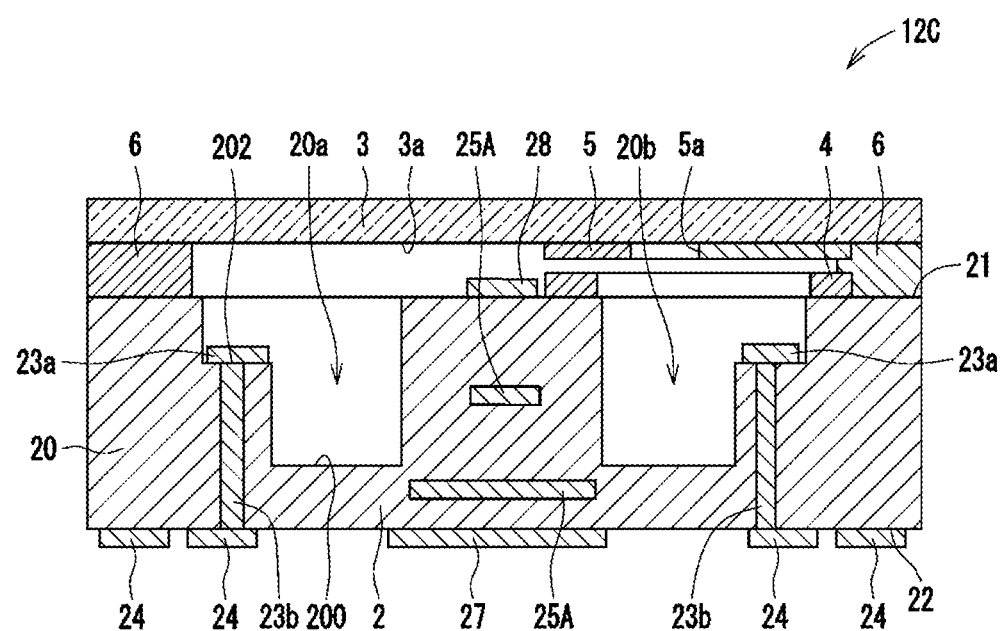
FIG. 12 is a cross-sectional view of a measurement sensor package 12C according to a fourth example of the second embodiment corresponding to the cross-sectional view of FIG. 8.

FIG. 12 is a cross-sectional view of a measurement sensor package 12C according to a fourth example corresponding to the cross-sectional view of FIG. 8.

The measurement sensor package 12C according to the fourth example basically has the same structure as the measurement sensor package 12 except that the measurement sensor package 12C includes a surface ground conductor layer 28 and a back surface ground conductor layer 27, and that a first internal ground conductor layer 25A is also between a second main surface (a second surface of a substrate 2) 22 of a substrate body 20 and a first bottom surface 200 in its cross-section. The same components are given the same reference signs as for the measurement sensor package 12, and will not be described in detail.

The back surface ground conductor layer 27 is a conductive layer arranged on the second main surface (the second surface of the substrate 2) 22 of the substrate body 20. The back surface ground conductor layer 27 is arranged between a first recess 20a and a second recess 20b as viewed through from above. The back surface ground conductor layer 27 is formed from a conductive material and receives a ground potential.

The back surface ground conductor layer 27 may be, for example, circular, square, or rectangular, or in any other shape as viewed from above. The back surface ground conductor layer 27 in a fourth embodiment is elongated in a direction perpendicular to a direction linking the centroids of the first recess 20a and the second recess 20b as viewed through from above. The back surface ground conductor layer 27 may be located at least partially between the first recess 20a and the second recess 20b as viewed through from above, and may overlap the first recess 20a or the second recess 20b as viewed through from above.

As described above, external connection terminals 24, which are electrically connected to a light emitter or a light receiver, are arranged on the second main surface 22 of the substrate body 20 and electrically connected to a connection terminal on an external mounting board. Each external connection terminal 24 has a relatively large area to achieve strong mechanical connection with the connection terminal on the external mounting board. This may cause electromagnetic noise in a driving current for driving the light emitter to enter the external connection terminal 24 electrically connected to the light receiver. This may cause electric crosstalk between the light emitter and the light receiver.

The measurement sensor package 12C according to the fourth example including the above back surface ground conductor layer 27 prevents electromagnetic noise in the driving current for driving the light emitter from entering the external connection terminal 24 electrically connected to the light receiver. This reduces electric crosstalk between the light emitter and the light receiver and thus improves the accuracy of measurement.

Also, electromagnetic noise in the driving current for driving the light emitter may propagate toward a lid 3. Such electromagnetic noise may be reflected by the lid 3 and enter the light receiver. This may cause electric crosstalk between the light emitter and the light receiver. The measurement sensor package 12C according to the fourth embodiment including the above surface ground conductor layer 28 prevents such electromagnetic noise reflected by the lid 3 from entering the light receiver.

The measurement sensor package 12C also includes first internal ground conductor layers 25A, in addition to between the first bottom surface 200 and the first step surface 202, between the second main surface (second surface) 22 of the substrate body 20 and the first bottom surface 200 as viewed through laterally. The measurement sensor is mounted on the external mounting board for use. The external mounting board may allow any electromagnetic noise in the light emitter to enter the light receiver through the wiring, and may cause electric crosstalk between the light emitter and the light receiver. The measurement sensor package 12C uses the first internal ground conductor layer 25A arranged between the second surface 22 of the substrate body 20 and the first bottom surface 200 to prevent any electromagnetic noise in the light emitter from entering the light receiver through the wiring of the external mounting board.

Any structures combining the above embodiments or examples fall within the embodiments of the disclosure. For example, the structure according to one or more embodiments of the disclosure may include multiple first internal ground conductor layers 25A arranged at height positions that fall between the first bottom surface 200 and the first step surface 202 as well as at height positions between the first surface 21 of the substrate body 20 and the first step surface 202 as viewed through laterally, and may include at least either the surface ground conductor layer 28 or the back surface ground conductor layer 27.

A method for manufacturing the measurement sensor package 12 will now be described. First, the substrate 2 is fabricated using the same method as used for the measurement sensor package 11 described above.

The metallic thin layer 5 is then prepared with the same method as for the measurement sensor package 11.

Fifth Example

Figure 13:
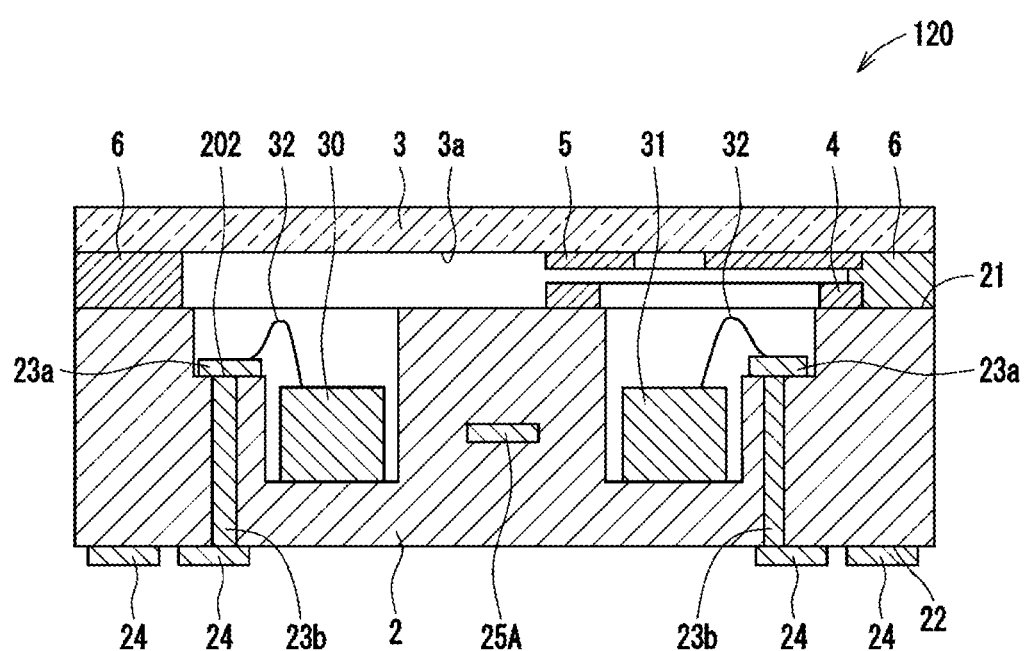
FIG. 13 is a cross-sectional view of a measurement sensor 120 showing its structure.

A measurement sensor 120 according to a fifth example of the present embodiment will now be described. FIG. 13 is a cross-sectional view of the measurement sensor 120 showing its structure. The measurement sensor 120 includes the above measurement sensor package 12, 12A, 12B, or 12C, a light emitter 30 accommodated in a first recess 20a, and a light receiver 31 accommodated in a second recess 20b. The measurement sensor 120 is obtained by mounting the light emitter 30 and the light receiver 31 on the measurement sensor package 12 and connecting the light emitter 30 and the light receiver 31 to connection pads 23a both using bonding wires 32, and joining a lid 3 to a substrate body 20 with a bond 6. FIG. 13 shows the measurement sensor 120 including the measurement sensor package 12.

The measurement sensor 120 is mounted on an external mounting board for use. For example, a control unit for controlling light emission from the light emitter 30, and an arithmetic unit that calculates the blood flow rate and other parameters based on signals output from the light receiver 31 are also mounted on the external mounting board.

The measurement sensor 120 uses the same method for measuring the blood flow rate and other parameters as for the measurement sensor 110 described above. An output signal from the light receiver 31 passes through the connection pad 23a and a signal via conductor 23b, and is output from the measurement sensor 120 to the external mounting board through an external connection terminal 24.

In the external mounting board, a signal output from the measurement sensor 120 is input to the arithmetic unit, which can then calculate the blood flow rate based on, for example, the frequency of the illuminating light emitted from the light emitter 30 and the frequency of the scattered light received by the light receiver 31.

The measurement sensor 120 according to the present embodiment includes the measurement sensor package 12, 12A, 12B, or 12C having a first internal ground conductor layer 25A, which prevents any electromagnetic noise in the light emitter from entering the light receiver. This structure reduces electric crosstalk between the light emitter and the light receiver, and thus improves the accuracy of measurement.

Other Examples

In one example, the measurement sensor package 12 shown in FIG. 8 underwent simulation for calculating the amount of crosstalk between the connection pad 23a on the first step surface 202 and the connection pad 23a on the second step surface 205. In the simulation, the components other than the substrate 2, the connection pad 23a on the first step surface 202, the connection pad 23a on the second step surface 205, and the first internal ground conductor layer 25A were excluded, and the substrate 2 is assumed to be a perfect conductor. The connection pad 23a on the first step surface 202 has a longitudinal dimension of 1.0 mm and a lateral dimension of 0.5 mm. The connection pad 23a on the second step surface 205 has a longitudinal dimension of 1.0 mm and a lateral dimension of 0.5 mm. The first internal ground conductor layer 25A has a longitudinal dimension of 1.2 mm and a lateral dimension of 0.4 mm. The connection pads 23a on the first step surface 202 and the second step surface 205 have a distance of 2.5 mm between their centers as viewed through from above. The connection pad 23a on the first step surface 202 and the first internal ground conductor layer 25A have a distance of 1.25 mm between their centers as viewed through from above.

Under the above conditions, the frequency dependence of the amount of crosstalk between the connection pads 23a on the first step surface 202 and the second step surface 205 was calculated. The calculation method will be described in detail below. A voltage signal output from the connection pad 23a on the second step surface 205 in response to an input voltage signal to the connection pad 23a on the first step surface 202 was calculated. The logarithm of the ratio of the strength of the output voltage signal to the strength of the input voltage signal was multiplied by a predetermined coefficient to obtain the amount of crosstalk. The frequency dependence of the amount of crosstalk was calculated by varying the frequency of the input voltage in the range of 1 to 20 kHz. In this simulation, a larger absolute value of the amount of crosstalk indicates more efficient electrical shielding between the connection pad 23a on the first step surface 202 and the connection pad 23a on the second step surface 205, and thus less electric crosstalk between the connection pads 23a on the first step surface 202 and the second step surface 205.

The frequency dependence of the amount of crosstalk between the connection pads 23a on the first step surface 202 and the second step surface 205 was calculated for a measurement sensor package according to a comparative example with basically the same structure as the measurement sensor package of the above example except that the first internal ground conductor layer 25A is eliminated.

Figure 14A:
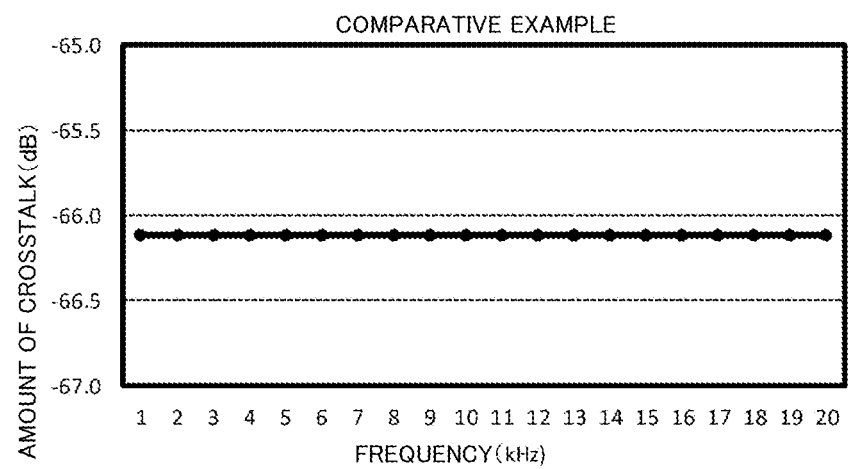
FIGS. 14A and 14B are graphs showing the simulation results for the amount of crosstalk in examples and comparative examples.
Figure 14B:
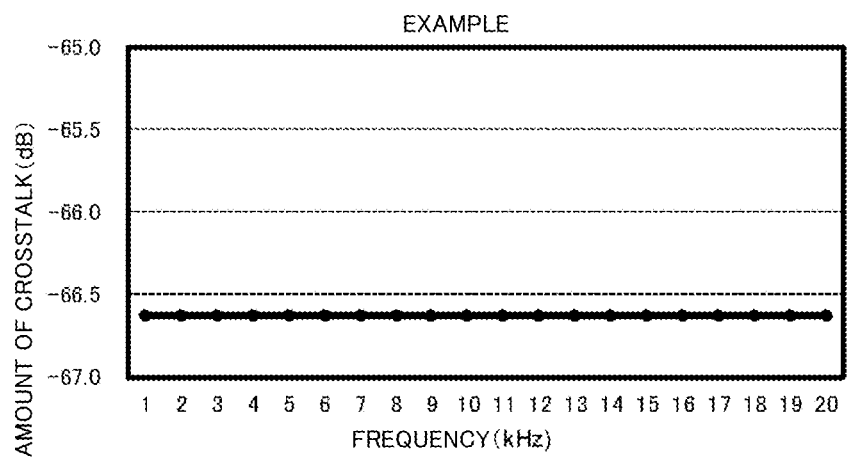

FIGS. 14A and 14B show the simulation results for the above examples and the comparative example. FIG. 14A shows the results for the comparative example. FIG. 14B shows the results for the above examples. As shown in FIGS. 14A and 14B, the results for the comparative example and the above other examples all reveal no dependency of the amount of crosstalk on the frequency of the input voltage. As shown in FIGS. 14A and 14B, the amount of crosstalk is smaller in the examples than in the comparative example within the full frequency bandwidth of 1 to 20 kHz.

Figure 15:
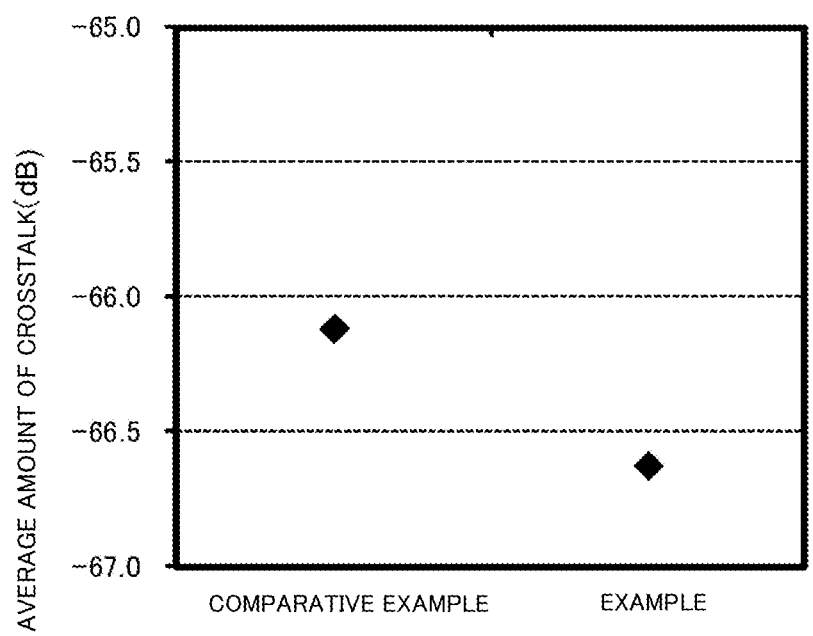
FIG. 15 is a graph showing the evaluation results in the examples and the comparative examples.

FIG. 15 is a graph showing the evaluation results for the above other examples and the comparative example. The average amount of crosstalk is used as the evaluation result. The average amount of crosstalk is the average amount of crosstalk across the frequency bandwidth of 1 to 20 kHz. A smaller absolute value of the average amount of crosstalk indicates more electric crosstalk. A larger absolute value of the average amount of crosstalk indicates less electric crosstalk. As shown in FIG. 15, less crosstalk is observed in the above other examples than in the comparative example.

As described above, the structures of the above examples including the first internal ground conductor layer 25A can reduce electric crosstalk between the connection pads 23a on the first step surface 202 and the second step surface 205.

Third Embodiment

FIG. 1 is a plan view of a measurement sensor package 13 according to a third embodiment of the present disclosure.

Figure 16:
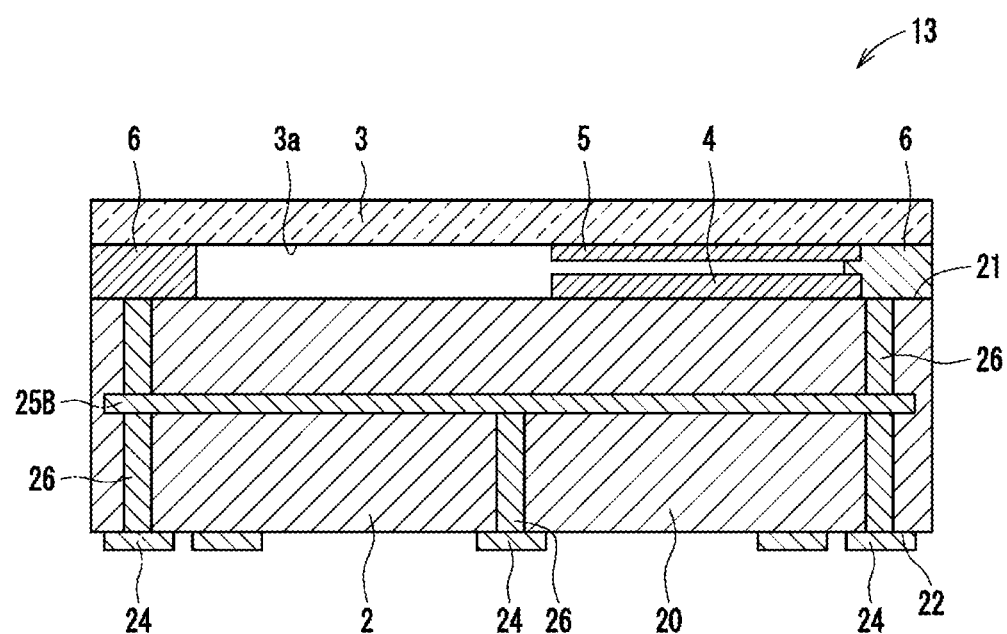
FIG. 16 is a cross-sectional view of a measurement sensor package 13 taken along line A-A of FIG. 1.
Figure 17:
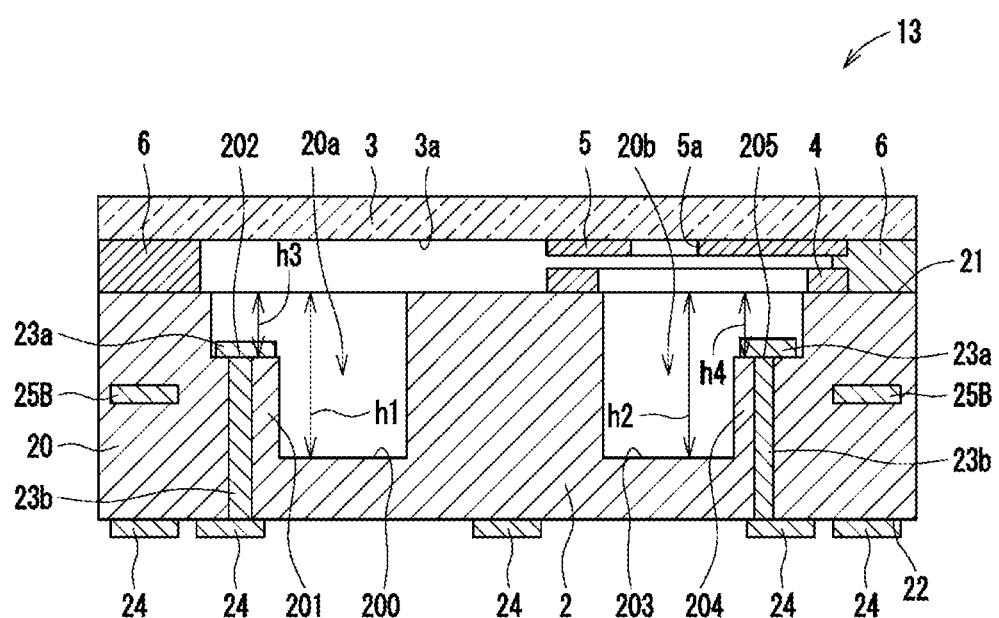
FIG. 17 is a cross-sectional view of the measurement sensor package 13 taken along line B-B of FIG. 1.

FIG. 16 is a cross-sectional view of the measurement sensor package 13 taken along line A-A of FIG. 1. FIG. 17 is a cross-sectional view of the measurement sensor package 13 taken along line B-B of FIG. 1.

The measurement sensor package 13 includes a substrate 2, a lid 3, a ground conductor layer (or a surface layer ground conductor layer) 4, a metallic thin layer 5, and a bond (or a conductive bond) 6. The substrate 2 accommodates a light emitter and a light receiver. The substrate 2 includes a substrate body 20 on which signal wiring conductors 23, external connection terminals 24, a second internal ground conductor layer 25B, and ground via conductors 26 are arranged.

The measurement sensor package 13 according to the present embodiment basically has the same structure as the above measurement sensor package 11 except that the measurement sensor package 13 includes the second internal ground conductor layer 25B with shielding against unintended external electromagnetic waves. The same components are given the same reference signs as for the measurement sensor package 11, and will not be described in detail.

First Example

The measurement sensor package 13 in the present embodiment has basically the same structure as the above measurement sensor package 11, and may be used for a measurement sensor that measures fluid flow such as blood flow using the Doppler effect of light.

Each signal wiring conductor 23 is electrically connected to the light emitter or the light receiver to transmit electric signals input to the light emitter or output from the light receiver. Each signal wiring conductor 23 in the present embodiment includes a bonding wire, which is a connector connected to the light emitter or the light receiver, a connection pad (or an electrode pad) 23a, to which the bonding wire is connected, a signal via conductor 23b, which is electrically connected to the connection pad 23a and extends from immediately below the connection pad 23a to a second main surface 22 as a second surface through the substrate body 20, and the external connection terminal 24, which is electrically connected to the signal via conductor 23b. Each external connection terminal 24 is arranged on the second main surface 22 of the substrate body 20 and electrically connected, with a terminal bond material such as solder, to a connection terminal for signals on an external mounting board, on which the measurement sensor including the measurement sensor package 13 is mountable.

The second internal ground conductor layer 25B is conductive, and is arranged between dielectric layers included in the substrate 2. The second internal ground conductor layer 25B is arranged outside a first recess 20a and a second recess 20b as viewed through from above. The second internal ground conductor layer 25B electrically connects to the ground via conductors 26. The ground via conductors 26 electrically connect to the external connection terminals 24 on the second main surface 22. Each external connection terminal 24 is electrically connected to a ground terminal on the external mounting board with a terminal bond material such as solder. Thus, the second internal ground conductor layer 25B receives a ground potential. When viewed through from above, the entire measurement sensor package 13 is viewed through in a direction perpendicular to a first main surface 21 (or the second main surface 22) of the substrate 2.

The second internal ground conductor layer 25B is arranged outside the first and second recesses 20a and 20b, and serves as a shield against unintended external electromagnetic waves. This reduces such electromagnetic waves reaching each signal wiring conductor 23, the light receiver, and the light emitter, which are located inward from the second internal ground conductor layer 25B. This reduces noise during measurement, and improves the accuracy of measurement.

As shown in FIG. 17, the second internal ground conductor layer 25B in the present embodiment is arranged between a first bottom surface 200 and a first step surface 202 (or between a second bottom surface 203 and a second step surface 205) as viewed through laterally. In other words, the second internal ground conductor layer 25B is arranged outside the first recess 20a and the second recess 20b as viewed through from above, and embedded in the substrate body 20 at a height position between the first bottom surface 200 and the first step surface 202. Viewing through laterally herein intends to mean viewing the entire measurement sensor package 13 through in a direction perpendicular to the thickness of the substrate 2, or specifically in a direction perpendicular to the direction in which the measurement sensor package 13 is viewed through from above.

The second internal ground conductor layer 25B in the present embodiment is arranged at a height position within the range defined above. The second internal ground conductor layer 25B is thus aligned with the light emitter and light receiver accommodated in the first and second recesses 20a and 20b in the horizontal direction. The second internal ground conductor layer 25B in the present embodiment arranged at such a height position particularly prevents external electromagnetic waves from reaching the light emitter and the light receiver, and thus reduces noise in the internal circuits in the light emitter and the light receiver. The structure according to the present embodiment may include multiple second internal ground conductor layers 25B at different height positions within the range defined above.

The external connection terminal 24 may be, for example, plated sequentially with a nickel layer having a thickness of 0.5 to 10 μm and a gold layer having a thickness of 0.5 to 5 μm to improve wettability with the bond, such as solder, and improve corrosion resistance.

The lid 3 is bonded to the first main surface (the first surface of the substrate 2) 21 of the substrate 2 with the bond 6 to cover the first main surface 21 of the substrate body 20.

A measurement sensor including the measurement sensor package 13 according to the present embodiment illuminates a finger, which is a measurement object, placed on the surface of the lid 3 with light emitted from the light emitter. In the measurement sensor package 13, similarly to the above measurement sensor package 11, the lid 3 may be formed from an insulating material, and thus does not allow unintended electric charge to flow through the lid 3.

The ground conductor layer 4 is a metallized layer on the first main surface 21 of the substrate body 20 to surround the opening of the second recess 20b for accommodating the light receiver. The ground conductor layer 4 may have, for example, a rectangular contour in conformance with the contour of the first main surface 21 of the substrate body 20, or may be in any other shape, such as circular or polygonal. The ground conductor layer 4 in the present embodiment has a rectangular contour. The ground conductor layer 4 is a metallized layer surrounding the opening of the second recess 20b. Thus, the ground conductor layer 4 may have a through-hole with at least the same shape as the opening or larger than the opening.

The ground conductor layer 4 is connected to, for example, the ground via conductors 26 included in the substrate 2 or the bond 6 (described later), and receives a ground potential. The ground conductor layer 4 is arranged on the first main surface 21 of the substrate body 20. The ground conductor layer 4 thus on the surface of the substrate 2 is electrically connected to the metallic thin layer 5 with the bond 6. As a result, the metallic thin layer 5 receives a ground potential. This allows the metallic thin layer 5 to serve as an electric shield against an external charged object (specifically, a measurement object such as a finger), and thus prevent noise from entering the light receiver 31.

The metallic thin layer 5 reduces susceptibility to optical and electrical noise, and improves the measurement accuracy. The metallic thin layer 5 may be electrically connected to the ground conductor layer 4 and receive a ground potential. Although the metallic thin layer 5 and the ground conductor layer 4 have the contours with the same size, they may have contours with different sizes.

In the present embodiment, the ground conductor layer 4 and the metallic thin layer 5 are arranged inside the periphery of the bond 6 extending continuously as viewed through from above. In other words, the ground conductor layer 4 and the metallic thin layer 5 partially extend in the area between the first main surface 21 of the substrate body 20 and the facing surface 3a of the lid 3. The lid 3 and the substrate 2 are directly bonded together along the entire periphery by the bond 6. The bond 6 may be arranged to partially overlap the ground conductor layer 4 or the metallic thin layer 5.

The substrate 2 and the lid 3 bonded together can increase the bonding strength in the area without the ground conductor layer 4 and the metallic thin layer 5 between them, and thus prevent, for example, the lid 3 from coming off.

Second and Third Examples

Figure 18:
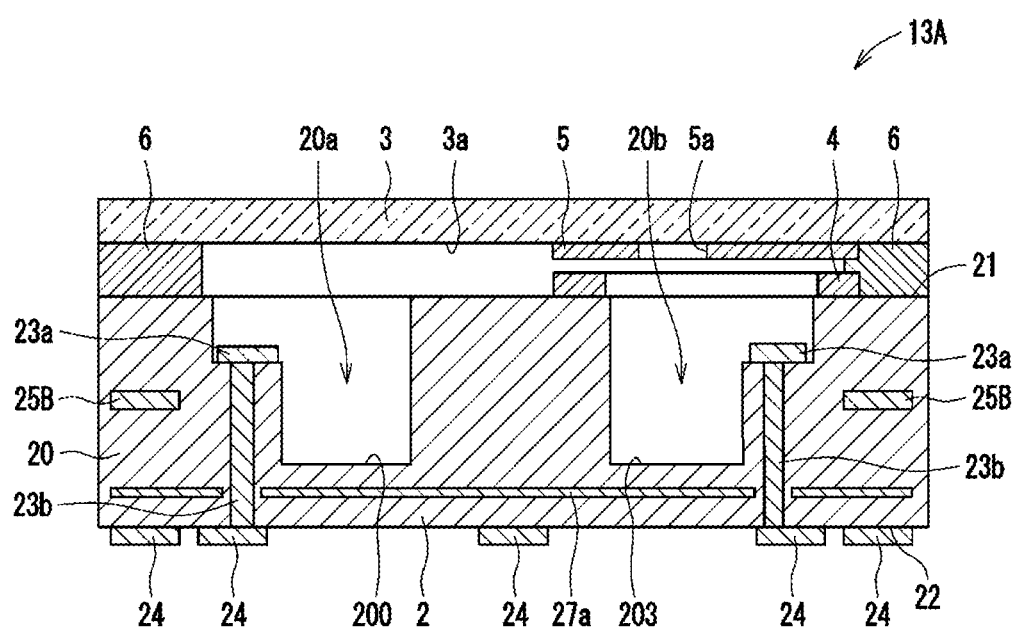
FIG. 18 is a cross-sectional view of a measurement sensor package 13A according to a second example of a third embodiment corresponding to the cross-sectional view of FIG. 17.
Figure 19:
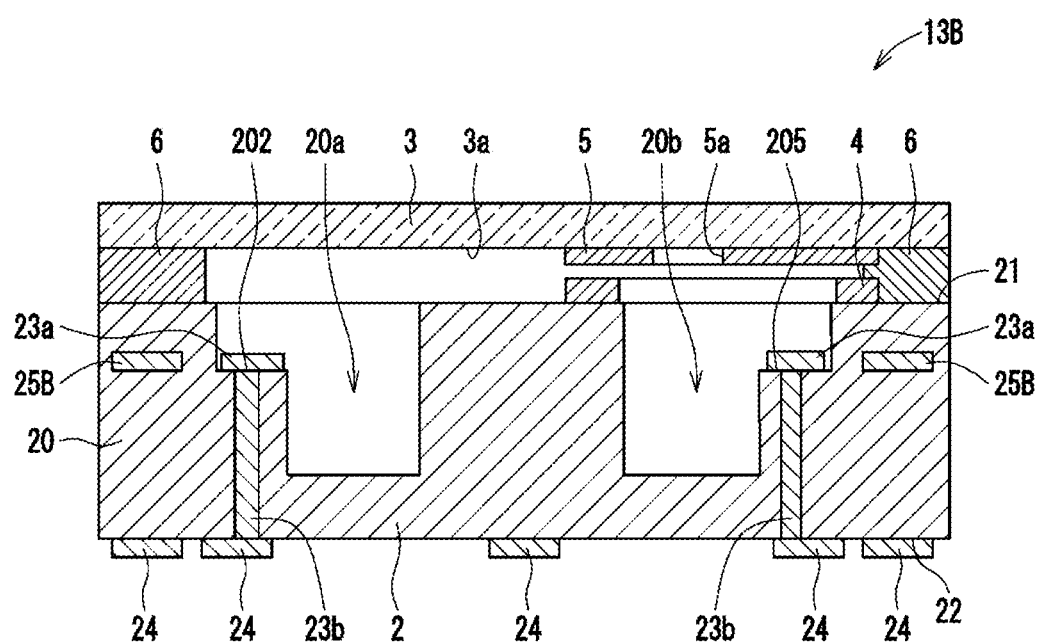
FIG. 19 is a cross-sectional view of a measurement sensor package 13B according to a third example of the third embodiment corresponding to the cross-sectional view of FIG. 17.

Other examples of the present embodiment will now be described. FIG. 18 is a cross-sectional view of a measurement sensor package 13A according to a second example corresponding to the cross-sectional view of FIG. 17. FIG. 19 is a cross-sectional view of a measurement sensor package 13B according to a third example corresponding to the cross-sectional view of FIG. 17.

The measurement sensor package 13A according to the second example basically has the same structure as the above measurement sensor package 13 except that the measurement sensor package 13A further includes a bottom ground conductor layer 27a. The same components are given the same reference signs as for the measurement sensor package 13, and will not be described in detail.

The bottom ground conductor layer 27a is a solid ground layer connected to the ground potential and arranged across a substantially entire area between a first bottom surface 200 of a first recess 20a and a second main surface 22, and a second bottom surface 203 of a second recess 20b and the second main surface 22 in a substrate body 20. The bottom ground conductor layer 27a is electrically connected to ground via conductors 26 in the substrate body 20 and receives a ground potential.

The measurement sensor is mounted on an external mounting board for use. An electromagnetic wave resulting from, for example, signals flowing through the wiring of the external mounting board may enter the measurement sensor package 13A through a second main surface 22 of the substrate body 20, and may generate noise in signals flowing through signal wiring conductors 23.

The bottom ground conductor layer 27a located between the first and second recesses 20a and 20b and the external mounting board serves as an electromagnetic shield.

The measurement sensor package 13B according to the present embodiment basically has the same structure as the above measurement sensor package 13 except that a second internal ground conductor layer 25B is at a different height position in a substrate body 20. The same components are given the same reference signs as for the measurement sensor package 13, and will not be described in detail.

The measurement sensor package 13B according to the present embodiment includes the second internal ground conductor layer 25B arranged between a first main surface (first surface) 21 and a first step surface 202, or the first main surface (first surface) 21 and a second step surface 205 as viewed through laterally. In other words, the second internal ground conductor layer 25B is arranged outside first and second recesses 20a and 20b as viewed through from above, and embedded in a substrate body 20 at a height position between the heights of the first main surface 21 and the first step surface 202 as viewed through from above.

The second internal ground conductor layer 25B in the present embodiment is arranged at the above height position. The second internal ground conductor layer 25B is thus aligned with bonding wires, which each are connected to the light emitter and light receiver accommodated in the first and second recesses 20a and 20b, in the horizontal direction. The second internal ground conductor layer 25B in the present embodiment arranged at such a height position particularly prevents external electromagnetic waves from reaching the bonding wires, and thus reduces noise in the bonding wires. The structure according to the present embodiment may include multiple second internal ground conductor layers 25B at different height positions within the range defined above.

Figure 20:
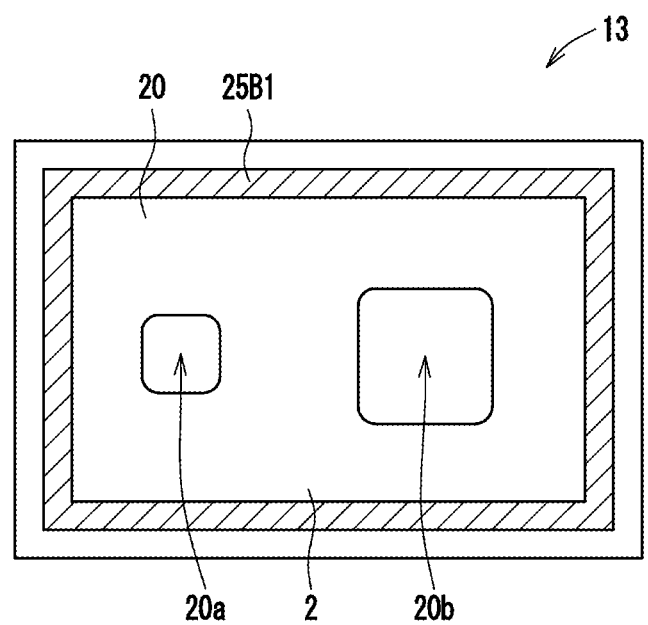
FIG. 20 is a perspective plan view of a second internal ground conductor layer 25B1 of the measurement sensor package 13.
Figure 21:
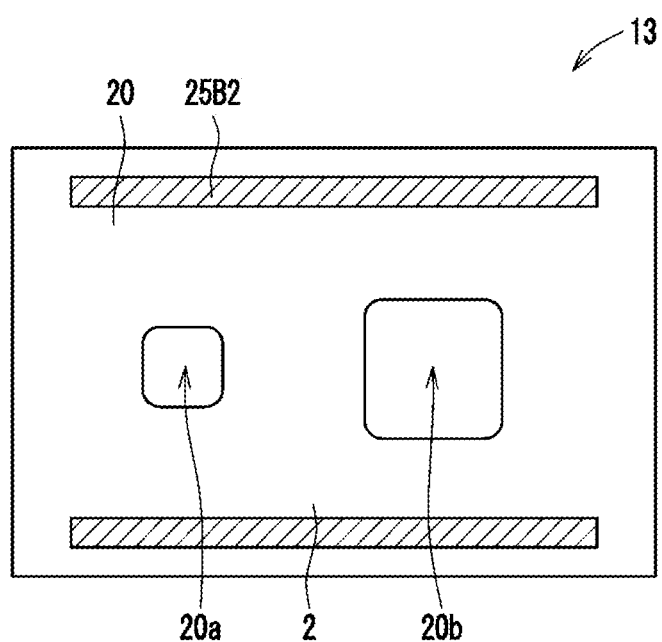
FIG. 21 is a perspective plan view of a second internal ground conductor layer 25B2 of the measurement sensor package 13.
Figure 22:
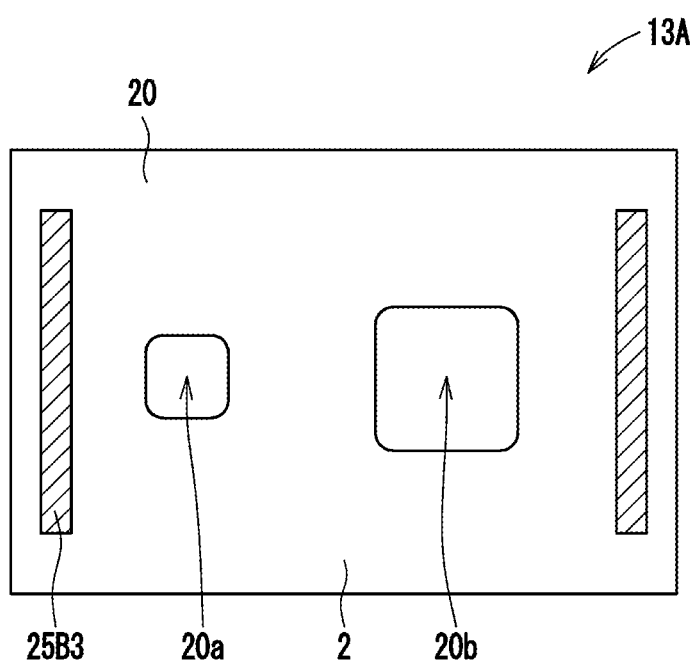
FIG. 22 is a perspective plan view of a second internal ground conductor layer 25B3 of the measurement sensor package 13.

The second internal ground conductor layer 25B may be, but not limited to, a strip or be wire-like as shown in the perspective plan views in FIGS. 20 to 22 when the second internal ground conductor layer 25B can be arranged outside the first and second recesses 20a and 20b as viewed through from above. In FIGS. 20 to 22, second internal ground conductor layers 25B1 to 25B3 are hatched for purposes of illustration.

For example, the second internal ground conductor layer 25B1 shown in FIG. 20 extends continuously along the four sides of the first main surface 21 of the substrate 2 as viewed through from above. The second internal ground conductor layer 25B1 extends continuously and thus serves as an electromagnetic shield against electromagnetic waves in any direction across the measurement sensor package 13.

For example, the second internal ground conductor layer 25B2 shown in FIG. 21 includes two parallel wiring portions along the long sides of the first main surface 21 of the substrate 2 as viewed through from above. The second internal ground conductor layer 25B2 serves as an electromagnetic shield particularly against electromagnetic waves from the long sides.

For example, the second internal ground conductor layer 25B3 shown in FIG. 22 includes two parallel wiring portions along the short sides of the first main surface 21 of the substrate 2 as viewed through from above. The second internal ground conductor layer 25B3 serves as an electromagnetic shield particularly against electromagnetic waves from the short sides.

The second internal ground conductor layers 25B in the first to third examples described above have their designs limited only by the arrangement of, for example, other wirings or recesses, and may have any shapes and sizes. The second internal ground conductor layers 25B1 to 25B3 illustrated in FIGS. 20 to 22 may be combined with the structures according to any of the first to third examples of the embodiments.

Embodiments of the present disclosure may include structures combining the first to third examples. For example, the second internal ground conductor layer 25B may be arranged at a height position between the first main surface 21 and the first step surface 202 in addition to at a height position between the first bottom surface 200 and the first step surface 202 as viewed through laterally. This structure may further include the bottom ground conductor layer 27a. As described in the second example, the second internal ground conductor layer 25B2 may be arranged at a height position between the first main surface 21 and the first step surface 202 as viewed through laterally, and may further be combined with the bottom ground conductor layer 27a.

A method for manufacturing the measurement sensor package 13 will now be described. First, the substrate 2 is fabricated using the same method as used for the measurement sensor package 11 described above.

The metallic thin layer 5 is then prepared with the same method as for the measurement sensor package 11.

Fourth Example

Figure 23:
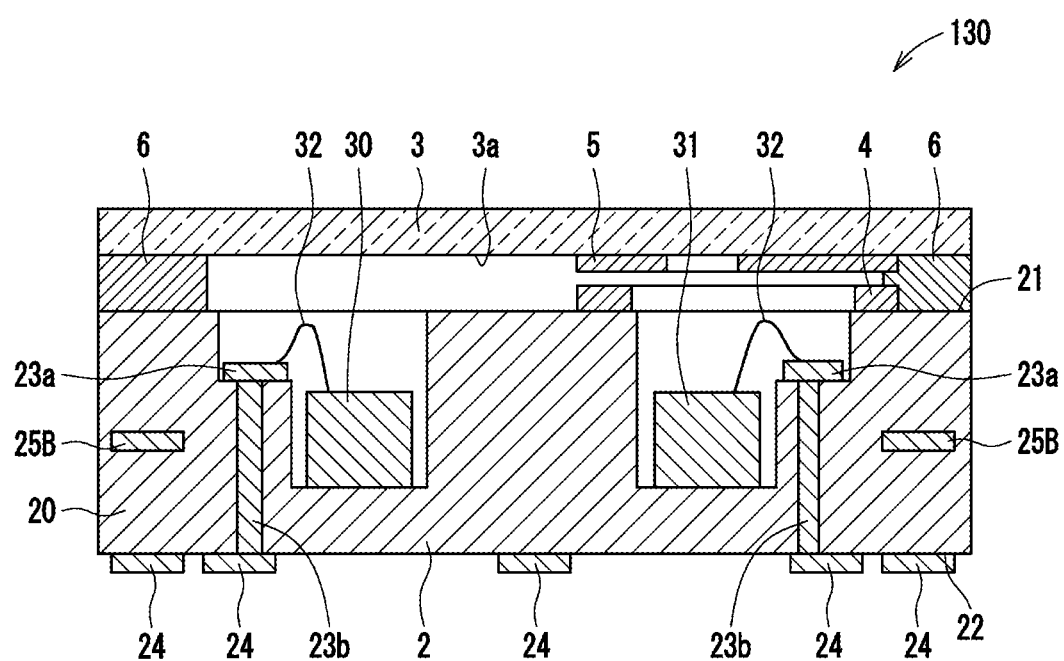
FIG. 23 is a cross-sectional view of a measurement sensor 130 showing its structure.

A measurement sensor 130 according to a fourth example of the present embodiment will now be described. FIG. 23 is a cross-sectional view of the measurement sensor 130 showing its structure. The measurement sensor 130 includes the measurement sensor package 13, 13A, or 13B, a light emitter 30 accommodated in a first recess 20a, and a light receiver 31 accommodated in a second recess 20b. The measurement sensor 130 is obtained by mounting the light emitter 30 and the light receiver 31 on the measurement sensor package 13 and connecting the light emitter 30 and the light receiver 31 to connection pads 23a both using bonding wires 32, and joining a lid 3 to a substrate body 20 with a bond 6.

The measurement sensor 130 is mounted on an external mounting board for use. For example, a control unit for controlling light emission from the light emitter 30, and an arithmetic unit that calculates the blood flow rate and other parameters based on signals output from the light receiver 31 are also mounted on the external mounting board.

The measurement sensor 130 uses the same method for measuring the blood flow rate and other parameters as for the measurement sensor 120 described above. An output signal from the light receiver 31 passes through the connection pad 23a and a signal via conductor 23b, and is output from the measurement sensor 130 to the external mounting board through an external connection terminal 24.

In the external mounting board, a signal output from the measurement sensor 130 is input to the arithmetic unit, which can then calculate the blood flow rate based on, for example, the frequency of the illuminating light emitted from the light emitter 30 and the frequency of the scattered light received by the light receiver 31.

Ground via conductors 26 connected to a second internal ground conductor layer 25B may connect between the bond 6 and the external connection terminals 24. The ground via conductors 26 thus guide electric charge from a human finger as a measurement object touching the measurement sensor from a first main surface 21 to a second main surface 22 of the substrate body 20, and then outside.

The ground via conductors 26 define a path that allows electric charge from a human to easily flow in the measurement sensor package 13 to guide the electric charge on the path and then outside. This reduces electrical noise.

Fourth Embodiment

Figure 24:
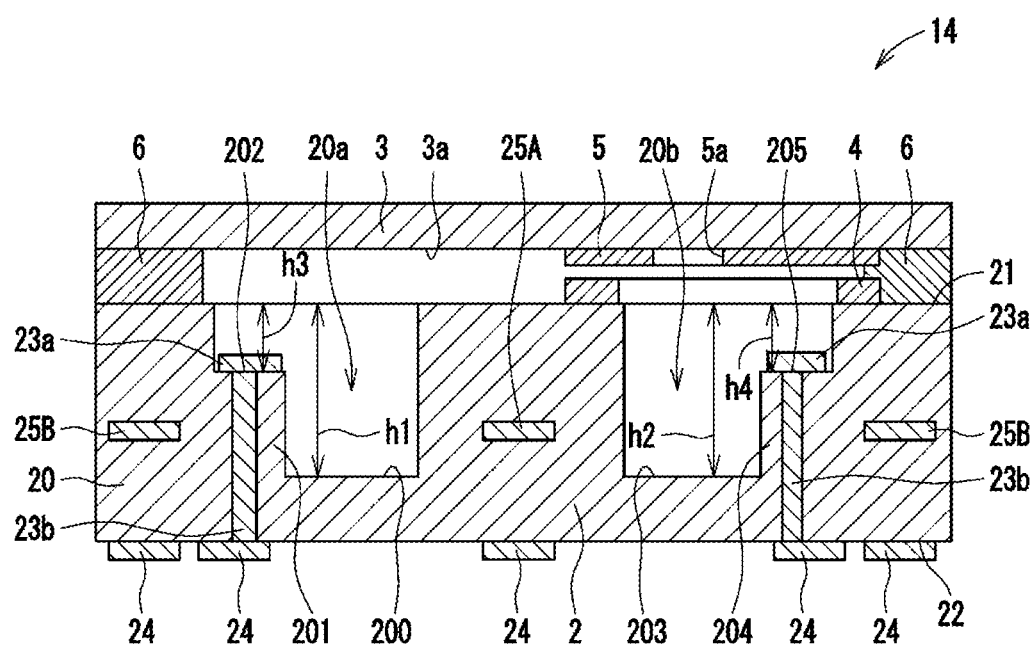
FIG. 24 is a cross-sectional view of a measurement sensor package 14 taken along line B-B of FIG. 1.

As descried above, FIG. 1 is a plan view of a measurement sensor package 14 according to a fourth embodiment of the present disclosure. FIG. 24 is a cross-sectional view of the measurement sensor package 14 taken along line B-B of FIG. 1. The measurement sensor package 14 according to the present embodiment further includes the first internal ground conductor layer 25A in the second embodiment and the second internal ground conductor layer 25B in the third embodiment in addition to the components of the measurement sensor package 11 according to the first embodiment.

As described above, the measurement sensor package 14 combines the above measurement sensor package 12 with the measurement sensor package 13, and thus includes the first internal ground conductor layer 25A as a shield against electromagnetic noise and the second internal ground conductor layer 25B as a shield against unintended external electromagnetic waves as described above. The same components are given the same reference signs as for the measurement sensor package 12 and the measurement sensor package 13, and will not be described in detail.

The measurement sensor package 14 in the present embodiment has basically the same structure as the above measurement sensor packages 12 and 13, and may be used for a measurement sensor that measures fluid flow such as blood flow using the Doppler effect of light.

The first internal ground conductor layer 25A is conductive, and is arranged between dielectric layers included in a substrate 2. The internal ground conductor layer 25A is arranged between a first recess 20a and a second recess 20b, and outside the first recess 20a and the second recess 20b as viewed through from above.

More specifically, the first internal ground conductor layer 25A is arranged on a path through which any electromagnetic noise in a light emitter propagates toward a light receiver. This structure effectively prevents such electromagnetic noise in the light emitter from entering the light receiver through a portion separating the first recess 20a and the second recess 20b in a substrate body 20. This effectively reduces electric crosstalk between the light emitter and the light receiver.

The second internal ground conductor layer 25B is arranged outside the first and second recesses 20a and 20b, and serves as a shield against unintended external electromagnetic waves. This reduces such electromagnetic waves reaching each signal wiring conductor 23, the light receiver, and the light emitter, which are located inward from the second internal ground conductor layer 25B. This reduces noise during measurement, and improves the accuracy of measurement.

Figure 25:
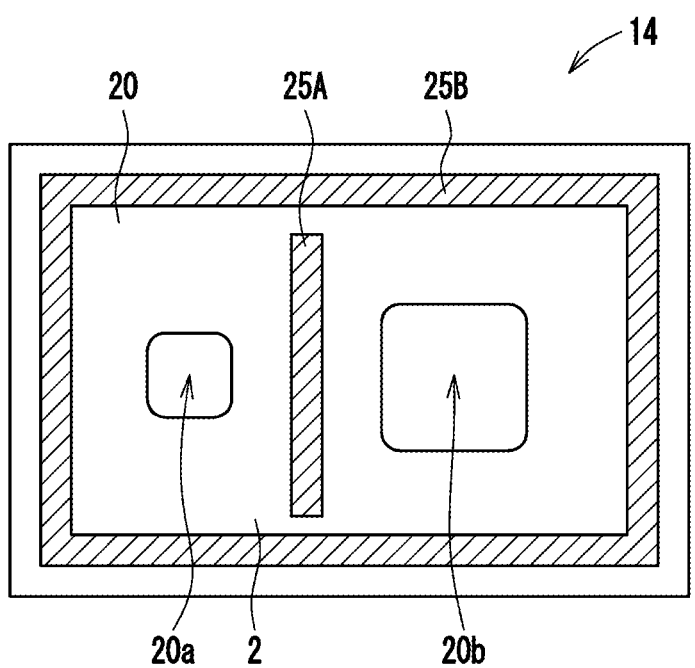
FIG. 25 is a perspective plan view of a first internal ground conductor layer 25A and a second internal ground conductor layer 25B of the measurement sensor package 14.

The first internal ground conductor layer 25A and the second internal ground conductor layer 25B may be, but not limited to, a strip or be wire-like as shown in the perspective plan view in FIG. 25 when the first and second internal ground conductor layers 25A and 25B can be arranged between and outside the first and second recesses 20a and 20b as viewed through from above. In FIG. 25, the first and second internal ground conductor layers 25A and 25B are hatched for purposes of illustration. FIG. 25 shows the second internal ground conductor layer 25B1 as a specific example of the second internal ground conductor layer 25B.

For example, the first internal ground conductor layer 25A shown in FIG. 25 is arranged in a direction intersecting with a direction linking the centroids of the first and second recesses 20a and 20b, and the second internal ground conductor layer 25B extends continuously along the four sides of a first main surface 21 of the substrate 2 as viewed through from above. As described above, the first and second internal ground conductor layers 25A and 25B more effectively prevent any electromagnetic noise in the light emitter from entering the light receiver. This structure more effectively reduces electric crosstalk between the light emitter and the light receiver, and serves as an electromagnetic shield against electromagnetic waves in any direction across the measurement sensor package 14.

A method for manufacturing the measurement sensor package 14 will now be described. First, the substrate 2 is fabricated using the same method as used for the measurement sensor packages 12 and 13 described above.

The metallic thin layer 5 is then prepared with the same method as for the measurement sensor package 11 described above.

Figure 26:
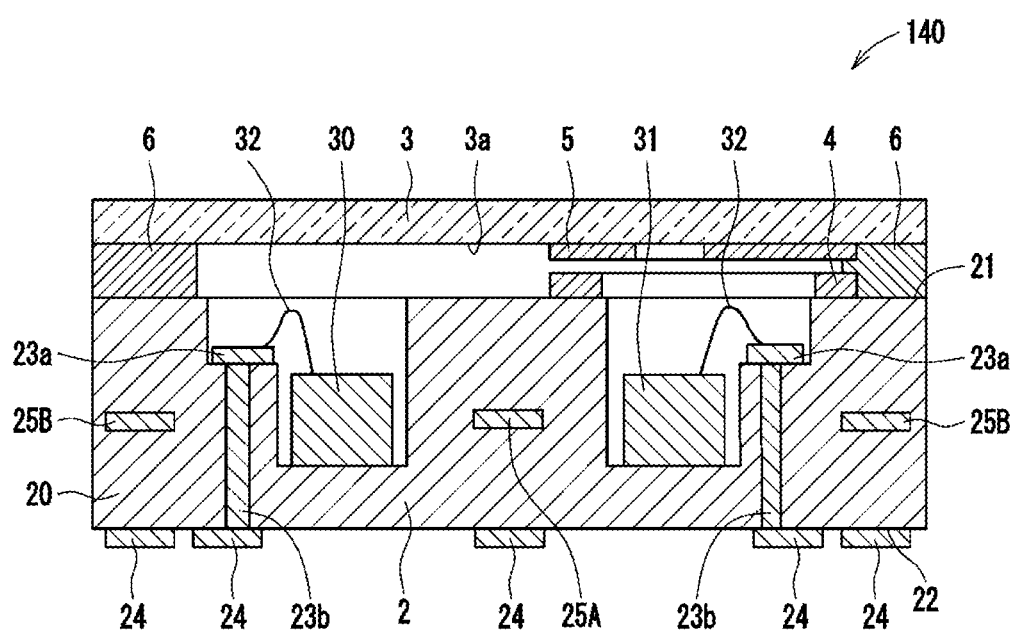
FIG. 26 is a cross-sectional view of a measurement sensor 140 showing its structure.

A measurement sensor 140 according to the present embodiment will now be described. FIG. 26 is a cross-sectional view of the measurement sensor 140 showing its structure. The measurement sensor 140 includes the above measurement sensor package 14, a light emitter 30 accommodated in a first recess 20a, and a light receiver 31 accommodated in a second recess 20b. The measurement sensor 140 is obtained by mounting the light emitter 30 and the light receiver 31 on the measurement sensor package 14 and connecting the light emitter 30 and the light receiver 31 to connection pads 23a both using bonding wires 32, and joining a lid 3 to a substrate body 20 with a bond 6.

The measurement sensor 140 is mounted on an external mounting board for use. For example, a control unit for controlling light emission from the light emitter 30, and an arithmetic unit that calculates the blood flow rate and other parameters based on signals output from the light receiver 31 are also mounted on the external mounting board. The measurement sensor 140 uses the same method for measuring the blood flow rate and other parameters as for the measurement sensors 120 and 130 described above. An output signal from the light receiver 31 passes through the connection pad 23a and a signal via conductor 23b, and is output from the measurement sensor 140 to the external mounting board through an external connection terminal 24.

In the external mounting board, a signal output from the measurement sensor 140 is input to the arithmetic unit, which can then calculate the blood flow rate based on, for example, the frequency of the illuminating light emitted from the light emitter 30 and the frequency of the scattered light received by the light receiver 31.

The present invention may be embodied in various forms without departing from the spirit or the main features of the present invention. The embodiments described above are thus merely illustrative in all respects. The scope of the present invention is defined not by the description given above but by the claims. Any modifications and alterations contained in the claims fall within the scope of the present invention.

REFERENCE SIGNS LIST 11, 11A, 11B, 14 measurement sensor package
12, 12A, 12B, 12C measurement sensor package
13, 13A, 13B measurement sensor package
2 substrate 3 lid
3a facing surface
4 ground conductor layer
5 metallic thin layer
5a aperture
6 bond
7 partition
20 substrate body
20a first recess
20b second recess
21 first main surface (first surface)
22 second main surface
21a first side
21b second side
22 second main surface (second surface)
23 signal wiring conductor
23a connection pad
23b signal via conductor
24 external connection terminal
25A first internal ground conductor layer
25B second internal ground conductor layer
25B1, 25B2, 25B3 second internal ground conductor layer
26 ground via conductor
27 back surface ground conductor layer
27a bottom ground conductor layer
28 surface ground conductor layer
30 light emitter
31 light receiver
32 bonding wire
41 ground conductor layer
42 lid ground conductor layer
43 surface layer ground conductor layer
110, 120, 130, 140 measurement sensor
200 first bottom surface
201 first step
202 first step surface
203 second bottom surface
204 second step
205 second step surface

The invention claimed is:

1. A measurement sensor package, comprising:
substrate with a plate-shaped including a plurality of dielectric layers stacked on one another, the substrate having a first surface with a first recess for accommodating a light emitter and a second recess for accommodating a light receiver;
a lid covering the first surface of the substrate, the lid with a plate-shaped comprising an insulating material and being optically transmissive;
a bond extending continuously along four sides of the first surface of the substrate and configured to bond the first surface of the substrate and a facing surface of the lid facing the first surface together, the bond being light-shielding;
a ground conductor layer surrounding an opening of the second recess on the substrate, the ground conductor layer being conductive;
a metallic thin layer on the lid, the metallic thin layer having an aperture to regulate light receivable by the light receiver; and
a partition between the first recess and the second recess on the first surface of the substrate, the partition being a strip extending from a first side of the first surface of the substrate toward a second side parallel to the first side, the partition being light-shielding.

2. The measurement sensor package according to claim 1, wherein
the ground conductor layer and the metallic thin layer are located in a segment defined by the partition and including the second recess.

3. The measurement sensor package according to claim 1, wherein
the metallic thin layer covers the ground conductor layer entirely as viewed through from above.

4. The measurement sensor package according to claim 1, further comprising:
a first internal ground conductor layer between the dielectric layers in the substrate, the first internal ground conductor being conductive and being located between the first recess and the second recess as viewed through from above.

5. The measurement sensor package according to claim 4, wherein
the first recess has a first bottom surface on which the light emitter is mountable, and has, on an inner side surface of the first recess, a first step including a first step surface on which an electrode pad electrically connectable to the light emitter is mounted,
the second recess has a second bottom surface on which the light receiver is mountable, and has, on an inner side surface of the second recess, a second step including a second step surface on which an electrode pad electrically connectable to the light receiver is mounted,
the first bottom surface and the second bottom surface are at the same distance from the first surface, and
the first step surface and the second step surface are at the same distance from the first surface.

6. The measurement sensor package according to claim 5, wherein
the first internal ground conductor layer is located between the first bottom surface and the first step surface as viewed through laterally.

7. The measurement sensor package according to claim 5, wherein
the first internal ground conductor layer is located between the first surface and the first step surface as viewed through laterally.

8. The measurement sensor package according to claim 1, wherein
the first internal ground conductor layer is elongated in a direction intersecting with a direction linking a centroid of the first recess and a centroid of the second recess as viewed through from above.

9. The measurement sensor package according to claim 1, further comprising:
a back surface ground conductor layer on a second surface of the substrate opposite to the first surface, the back surface ground conductor layer being located between the first recess and the second recess as viewed through from above.

10. The measurement sensor package according to claim 1, further comprising:
a surface ground conductor layer on the first surface, the surface ground conductor layer being located between the first recess and the second recess as viewed through from above.

11. The measurement sensor package according to claim 1, further comprising:
a second internal ground conductor layer between the dielectric layers in the substrate, the second internal ground conductor layer being conductive and being located outside the first recess and the second recess as viewed through from above.

12. The measurement sensor package according to claim 11, wherein
the first recess has a first bottom surface on which the light emitter is mountable, and has, on an inner side surface of the first recess, a first step including a first step surface on which an electrode pad electrically connectable to the light emitter is mounted,
the second recess has a second bottom surface on which the light receiver is mountable, and has, on an inner side surface of the second recess, a second step including a second step surface on which an electrode pad electrically connectable to the light receiver is mounted,
the first bottom surface and the second bottom surface are at the same distance from the first surface, and
the first step surface and the second step surface are at the same distance from the first surface.

13. The measurement sensor package according to claim 12, wherein
the second internal ground conductor layer is located between the first bottom surface and the first step surface as viewed through laterally.

14. The measurement sensor package according to claim 12, wherein
the second internal ground conductor layer is located between the first surface and the first step surface as viewed through laterally.

15. The measurement sensor package according to claim 11, wherein
the second internal ground conductor layer extends continuously along four sides of the first surface of the substrate as viewed through from above.

16. The measurement sensor package according to claim 4, further comprising:
a second internal ground conductor layer between the dielectric layers in the substrate, the second internal ground conductor layer being conductive and being located outside the first recess and the second recess as viewed through from above.

17. A measurement sensor, comprising:
the measurement sensor package according to claim 1;
a light emitter accommodated in the first recess; and
a light receiver accommodated in the second recess.

18. A measurement sensor package, comprising:
a substrate with a plate-shaped including a plurality of dielectric layers stacked on one another, the substrate having a first surface with a first recess for accommodating a light emitter and a second recess for accommodating a light receiver;
a lid covering the first surface of the substrate, the lid with a plate-shaped comprising an insulating material and being optically transmissive;
a bond extending continuously along four sides of the first surface of the substrate and configured to bond the first surface of the substrate and a facing surface of the lid facing the first surface together, the bond being light-shielding;
a ground conductor layer surrounding an opening of the second recess on the substrate, the ground conductor layer being conductive;
a metallic thin layer on the lid, the metallic thin layer having an aperture to regulate light receivable by the light receiver; and
a first internal ground conductor layer between the dielectric layers in the substrate, the first internal ground conductor being conductive and being located between the first recess and the second recess as viewed through from above.

* * * * *